US010655188B2

(12) United States Patent
Jarvius et al.

(10) Patent No.: US 10,655,188 B2
(45) Date of Patent: May 19, 2020

(54) METHOD FOR DETERMINING THE IDENTITY AND ANTIMICROBIAL SUSCEPTIBILITY OF A MICROORGANISM

(71) Applicant: Q-linea AB, Uppsala (SE)

(72) Inventors: Jonas Jarvius, Uppsala (SE); Jan Grawe, Uppsala (SE)

(73) Assignee: Q-Linea AB, Uppsala (CH)

( * ) Notice: Subject to any disclaimer, the term of this patent is extended or adjusted under 35 U.S.C. 154(b) by 143 days.

(21) Appl. No.: 15/318,261

(22) PCT Filed: Jun. 12, 2015

(86) PCT No.: PCT/EP2015/063173
§ 371 (c)(1),
(2) Date: Dec. 12, 2016

(87) PCT Pub. No.: WO2015/189390
PCT Pub. Date: Dec. 17, 2015

(65) Prior Publication Data
US 2017/0121759 A1    May 4, 2017

(30) Foreign Application Priority Data

Jun. 13, 2014 (GB) .................................. 1410585.2
Apr. 24, 2015 (GB) .................................. 1507056.8

(51) Int. Cl.
*C12P 19/34* (2006.01)
*C12Q 1/689* (2018.01)
*C12Q 1/18* (2006.01)
*C12Q 1/04* (2006.01)

(52) U.S. Cl.
CPC .............. *C12Q 1/689* (2013.01); *C12Q 1/04* (2013.01); *C12Q 1/18* (2013.01)

(58) Field of Classification Search
None
See application file for complete search history.

(56) References Cited

U.S. PATENT DOCUMENTS

| | | | |
|---|---|---|---|
| 4,666,850 A | 5/1987 | Mehl et al. | |
| 4,886,071 A | 12/1989 | Mehl et al. | |
| 5,143,854 A | 9/1992 | Pirrung et al. | |
| 5,183,994 A | 2/1993 | Bowles, Sr. et al. | |
| 5,217,876 A | 6/1993 | Turner et al. | |
| 5,405,783 A | 4/1995 | Pirrung et al. | |
| 5,445,934 A | 8/1995 | Fodor et al. | |
| 5,510,267 A | 4/1996 | Marshall | |
| 5,744,305 A | 4/1998 | Fodor et al. | |
| 5,770,394 A | 6/1998 | Berndt | |
| 5,789,173 A | 8/1998 | Peck et al. | |
| 5,817,508 A | 10/1998 | Berndt | |
| 5,945,334 A | 8/1999 | Besemer et al. | |
| 6,028,293 A | 2/2000 | Nagle et al. | |
| 6,083,763 A * | 7/2000 | Balch ................... | B01J 19/0046 422/105 |
| 6,096,532 A | 8/2000 | Armstrong et al. | |
| 6,143,495 A | 11/2000 | Lizardi et al. | |
| 6,183,960 B1 | 2/2001 | Lizardi | |
| 6,225,625 B1 | 5/2001 | Pirrung et al. | |
| 6,261,776 B1 | 7/2001 | Pirrung et al. | |
| 6,291,183 B1 | 9/2001 | Pirrung et al. | |
| 6,310,189 B1 | 10/2001 | Fodor et al. | |
| 6,329,143 B1 | 12/2001 | Stryer et al. | |
| 6,403,957 B1 | 6/2002 | Fodor et al. | |
| 6,406,844 B1 | 6/2002 | Pirrung et al. | |
| 6,630,308 B2 | 10/2003 | Stryer et al. | |
| 6,646,243 B2 | 11/2003 | Pirrung et al. | |
| 6,660,234 B2 | 12/2003 | Stryer et al. | |
| 6,747,143 B2 | 6/2004 | Stryer et al. | |
| 6,803,208 B2 | 10/2004 | Seaver et al. | |
| 7,008,788 B2 | 3/2006 | Schremp et al. | |

(Continued)

FOREIGN PATENT DOCUMENTS

EP        0122581 A2    10/1984
EP        0143329 A2    6/1985

(Continued)

OTHER PUBLICATIONS

AliFax SRL, "Alfred 60$^{AST}$—First Automated System for Bacterial Culture and Susceptibility Testing", Alifax SRL, Italy (2015) 2 pages.
Anderson, Rolfe C. et al., "A Miniature Integrated Device for Automated Multistep Genetic Assays", Nucleic Acids Research, vol. 28, No. 12 (2000) pp. i-vi.
Antson, D.-O. et al., "PCR-Generated Padlock Probes Detect Single Nucleotide Variation in Genomic DNA", Nucleic Acids Research, vol. 28, No. 12 (2000) pp. i-vi.
Baker, Zelma et al., "The Bactericidal Action of Synthetic Detergents", Walter G. Zoller Memorial Dental Clinic, the Department of Bacteriology and Parasitology, and the Department of Medicine, The University of Chicago (1941) pp. 611-620.
Baner, Johan et al., "Signal Amplification of Padlock Probes by Rolling Circle Replication", Nucleic Acids Reasearch, vol. 26, No. 22 (1998) pp. 5073-5078.

(Continued)

Primary Examiner — Kenneth R Horlick
(74) Attorney, Agent, or Firm — Fay Sharpe LLP

(57) ABSTRACT

A method for detecting and characterizing a microorganism in a clinical sample includes introducing a clinical sample to a first culture vessel containing the culture medium; removing a test aliquot; separating DNA from the test aliquot; and performing nucleic acid tests on the DNA to identify the microorganism and to detect the presence or absence of one or more genetic antimicrobial resistance markers in the microorganism. If a microorganism is identified, an antimicrobial susceptibility test is performed wherein microbial growth in the antimicrobial susceptibility test is monitored by accessing growth or markers for growth and wherein the type and concentration of antimicrobial agents used in the antimicrobial susceptibility test is determined by the identity of the microorganism and the antimicrobial resistance markers detected. A device for performing the method is also provided.

19 Claims, 8 Drawing Sheets

(56) References Cited

U.S. PATENT DOCUMENTS

Figure 1:
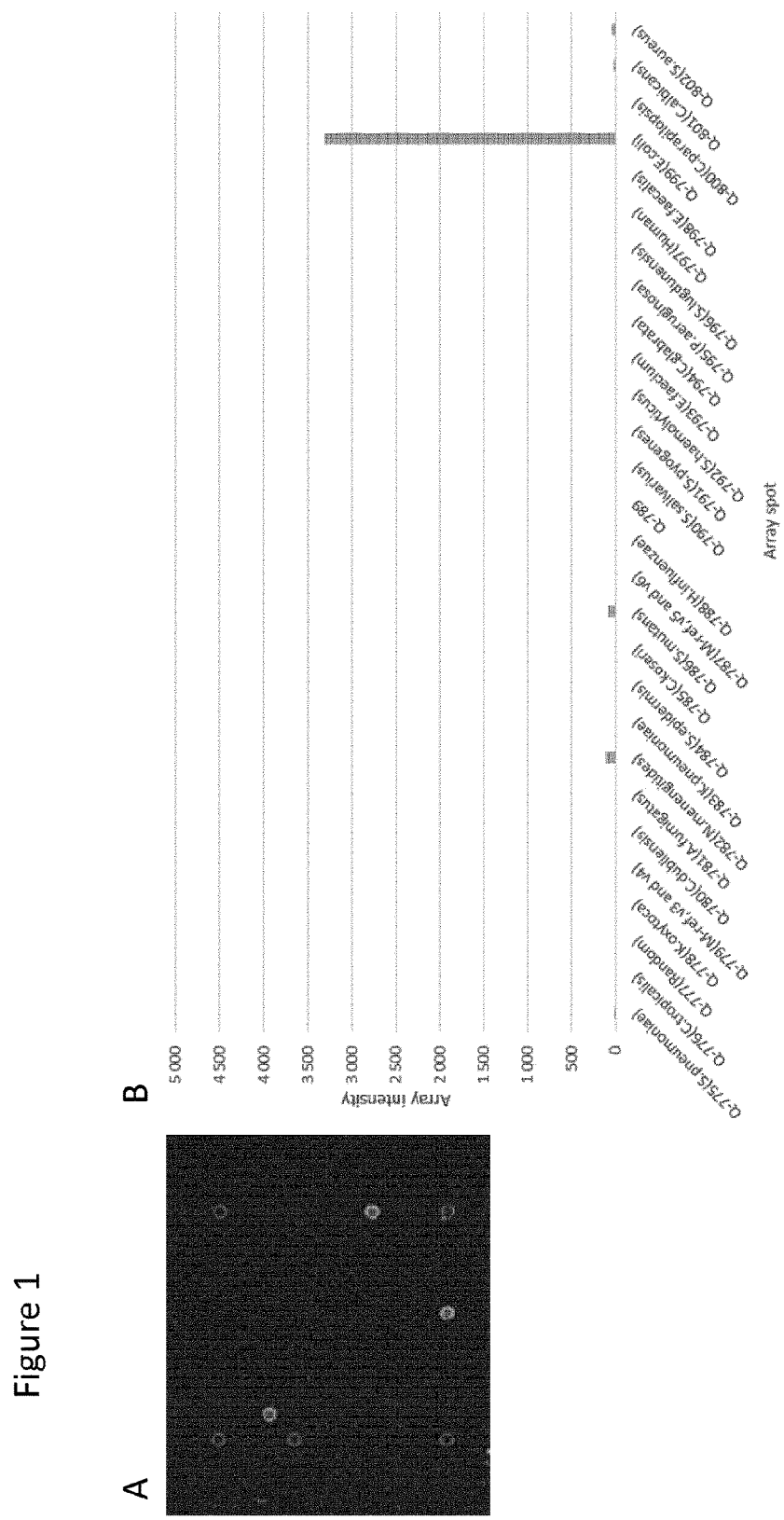

| | | |
|---|---|---|
| 7,087,732 B2 | 8/2006 | Fodor et al. |
| 7,223,363 B2 | 5/2007 | McNeely et al. |
| 7,235,400 B2 | 6/2007 | Adey |
| 7,341,841 B2 | 3/2008 | Metzger et al. |
| 7,387,883 B2 | 6/2008 | Walsh et al. |
| 7,547,526 B2 | 6/2009 | Ladisch et al. |
| 7,687,239 B2 | 3/2010 | Goldberg et al. |
| 7,790,388 B2 | 9/2010 | Landegren et al. |
| 7,893,251 B2 | 2/2011 | Lorenz |
| 8,071,319 B2 | 12/2011 | Metzger et al. |
| 8,074,465 B2 | 12/2011 | Heroux et al. |
| 8,288,522 B2 | 10/2012 | Luo et al. |
| 8,460,887 B2 | 6/2013 | Goldberg et al. |
| 8,481,265 B2 | 7/2013 | Peytavi et al. |
| 8,603,769 B2 | 12/2013 | Feng et al. |
| 8,609,024 B2 | 12/2013 | Ronsick et al. |
| 8,652,800 B2 | 2/2014 | Walsh et al. |
| 8,709,344 B2 | 4/2014 | Bishop et al. |
| 8,709,748 B2 | 4/2014 | Walsh et al. |
| 8,780,181 B2 | 7/2014 | Olesen et al. |
| 8,841,118 B2 | 9/2014 | Robinson et al. |
| 8,846,897 B2 | 9/2014 | Euting et al. |
| 8,895,255 B1 | 11/2014 | Goldberg et al. |
| 8,911,987 B2 | 12/2014 | Robinson et al. |
| 8,937,174 B2 | 1/2015 | Rothmann et al. |
| 2002/0055101 A1 | 5/2002 | Bergeron et al. |
| 2003/0098271 A1 | 5/2003 | Somack et al. |
| 2003/0235853 A1 | 12/2003 | Stryer et al. |
| 2005/0037408 A1 | 2/2005 | Christensen et al. |
| 2005/0064469 A1 | 3/2005 | Schulz et al. |
| 2005/0095665 A1 | 5/2005 | Williams et al. |
| 2005/0148027 A1 | 7/2005 | Pirrung et al. |
| 2005/0202487 A1 | 9/2005 | Klepp et al. |
| 2005/0214828 A1 | 9/2005 | Pirrung et al. |
| 2006/0029972 A1 | 2/2006 | Lorenz |
| 2006/0094034 A1* | 5/2006 | Brousseau ............ C12Q 1/689 |
| | | 435/6.15 |
| 2006/0223098 A1 | 10/2006 | Lane et al. |
| 2008/0029247 A1 | 2/2008 | Nozaki et al. |
| 2008/0145919 A1 | 6/2008 | Franklin et al. |
| 2008/0160528 A1 | 7/2008 | Lorenz |
| 2009/0209031 A1 | 8/2009 | Stopek |
| 2010/0124763 A1 | 5/2010 | Walsh et al. |
| 2010/0184210 A1 | 7/2010 | Rossmanith et al. |
| 2010/0255474 A1 | 10/2010 | Russwurm et al. |
| 2010/0288060 A1 | 11/2010 | Ronsick et al. |
| 2010/0291615 A1 | 11/2010 | Ronsick et al. |
| 2010/0291619 A1 | 11/2010 | Robinson et al. |
| 2010/0291669 A1 | 11/2010 | Robinson et al. |
| 2010/0297645 A1 | 11/2010 | Pierik et al. |
| 2010/0311108 A1 | 12/2010 | Bishop et al. |
| 2011/0092691 A1 | 4/2011 | Euting et al. |
| 2011/0124028 A1 | 5/2011 | Robinson et al. |
| 2011/0124029 A1 | 5/2011 | Remes et al. |
| 2011/0124030 A1 | 5/2011 | Philipak et al. |
| 2011/0124038 A1 | 5/2011 | Bishop et al. |
| 2011/0124096 A1 | 5/2011 | Philipak et al. |
| 2011/0125314 A1 | 5/2011 | Robinson et al. |
| 2012/0009577 A1 | 1/2012 | Luo et al. |
| 2012/0077206 A1 | 3/2012 | Metzger et al. |
| 2012/0149599 A1 | 6/2012 | Williams et al. |
| 2012/0231446 A1 | 9/2012 | Heckel et al. |
| 2013/0045532 A1 | 2/2013 | Hyman et al. |
| 2013/0065223 A1 | 3/2013 | Klein et al. |
| 2013/0071615 A1 | 3/2013 | Murata et al. |
| 2013/0171615 A1 | 7/2013 | Van Meerbergen et al. |
| 2013/0183717 A1 | 7/2013 | Marble et al. |
| 2013/0184446 A1 | 7/2013 | Marble et al. |
| 2013/0217063 A1 | 8/2013 | Metzger et al. |
| 2013/0224729 A1 | 8/2013 | Church et al. |
| 2013/0252271 A1 | 9/2013 | Ullery |
| 2013/0261196 A1 | 10/2013 | Diamond et al. |
| 2014/0072998 A1 | 3/2014 | Ronsick et al. |
| 2014/0087361 A1 | 3/2014 | Dobbelaer et al. |
| 2014/0278136 A1 | 9/2014 | Shamsheyeva et al. |
| 2014/0287408 A1 | 9/2014 | Su et al. |
| 2014/0323340 A1 | 10/2014 | Goldberg et al. |
| 2015/0031074 A1 | 1/2015 | Robinson et al. |
| 2015/0132793 A1 | 5/2015 | Penterman et al. |
| 2015/0225762 A1 | 8/2015 | Metzger et al. |
| 2015/0344973 A1 | 12/2015 | Rolfe et al. |
| 2016/0010138 A1 | 1/2016 | Shamsheyeva |
| 2016/0053219 A1 | 2/2016 | Walker et al. |
| 2016/0281130 A1 | 9/2016 | Dahl et al. |

FOREIGN PATENT DOCUMENTS

| | | |
|---|---|---|
| EP | 0745140 A2 | 12/1996 |
| EP | 0745849 A2 | 12/1996 |
| EP | 0834553 A2 | 4/1998 |
| EP | 0853658 A1 | 7/1998 |
| EP | 0853658 B1 | 7/1998 |
| EP | 0951565 A1 | 10/1999 |
| EP | 0964704 A1 | 12/1999 |
| EP | 1467815 A1 | 10/2004 |
| EP | 1527172 A1 | 5/2005 |
| EP | 1574583 A1 | 9/2005 |
| EP | 1648286 A2 | 4/2006 |
| EP | 1861495 A1 | 12/2007 |
| EP | 1945821 A1 | 7/2008 |
| EP | 2049677 A1 | 4/2009 |
| EP | 2056114 A1 | 5/2009 |
| EP | 2185681 A1 | 5/2010 |
| EP | 2208075 A2 | 7/2010 |
| EP | 2333105 A1 | 6/2011 |
| EP | 2430445 A2 | 3/2012 |
| EP | 2430456 A2 | 3/2012 |
| EP | 2430457 A2 | 3/2012 |
| EP | 2430459 A2 | 3/2012 |
| EP | 2430460 A2 | 3/2012 |
| EP | 2430461 A2 | 3/2012 |
| EP | 2501811 A1 | 9/2012 |
| EP | 2510123 A1 | 10/2012 |
| EP | 2571976 A1 | 3/2013 |
| EP | 2684947 A1 | 1/2014 |
| EP | 2718713 A1 | 4/2014 |
| EP | 2734280 A1 | 5/2014 |
| EP | 2828398 A1 | 1/2015 |
| EP | 2870233 A1 | 5/2015 |
| EP | 2872523 A2 | 5/2015 |
| EP | 2288701 B1 | 6/2015 |
| EP | 2893344 A1 | 7/2015 |
| EP | 2942394 A1 | 11/2015 |
| EP | 2971055 A1 | 1/2016 |
| EP | 3077541 A2 | 10/2016 |
| GB | 2055530 A | 3/1981 |
| GB | 2520765 A | 6/2015 |
| JP | H08285839 A | 11/1996 |
| JP | 2005-502354 A | 3/2004 |
| JP | 2006-525809 A | 11/2005 |
| JP | 2010-537650 A | 12/2010 |
| RU | 2 228 735 C2 | 1/2004 |
| WO | WO 84/02721 A1 | 7/1984 |
| WO | WO 86/00139 A1 | 1/1986 |
| WO | WO 88/06189 A1 | 8/1988 |
| WO | WO 93/16384 A1 | 8/1993 |
| WO | WO 97/12029 A1 | 4/1997 |
| WO | WO 00/71675 A1 | 11/2000 |
| WO | WO 00/72970 A1 | 12/2000 |
| WO | WO 01/12199 A2 | 2/2001 |
| WO | WO 2003022999 A2 | 3/2003 |
| WO | WO 03/059516 A1 | 7/2003 |
| WO | WO 03/097831 A1 | 11/2003 |
| WO | WO 2005017202 | 2/2005 |
| WO | WO 2005/027714 A2 | 3/2005 |
| WO | WO 2005/068647 A2 | 7/2005 |
| WO | WO 2005/093045 A2 | 10/2005 |
| WO | WO 2006/020579 A2 | 2/2006 |
| WO | WO 2006/092278 A1 | 9/2006 |
| WO | WO 2007/035504 A1 | 3/2007 |
| WO | WO 2007/033051 A2 | 9/2007 |
| WO | WO 2008/017097 A1 | 2/2008 |
| WO | WO 2009/015484 A1 | 2/2009 |
| WO | WO 2009/057014 A2 | 5/2009 |

(56) References Cited

FOREIGN PATENT DOCUMENTS

| | | |
|---|---|---|
| WO | WO 2009/098104 A1 | 8/2009 |
| WO | WO 2009/153299 A1 | 12/2009 |
| WO | WO 2010/048511 A1 | 4/2010 |
| WO | WO 2010/062356 A1 | 6/2010 |
| WO | WO 2010/132741 A2 | 11/2010 |
| WO | WO 2010/132746 A2 | 11/2010 |
| WO | WO 2010/132749 A2 | 11/2010 |
| WO | WO 2010/132780 A2 | 11/2010 |
| WO | WO 2010/132805 A2 | 11/2010 |
| WO | WO 2010/132823 A2 | 11/2010 |
| WO | WO 2010/132829 A2 | 11/2010 |
| WO | WO 2011/019874 A1 | 2/2011 |
| WO | WO 2011/061274 A1 | 5/2011 |
| WO | WO 2011/070507 A1 | 6/2011 |
| WO | WO 2011/144304 A1 | 11/2011 |
| WO | WO 2012/162133 A1 | 11/2012 |
| WO | WO 2012/168003 A1 | 12/2012 |
| WO | WO 2013/016211 A1 | 1/2013 |
| WO | WO 2013/142347 A1 | 9/2013 |
| WO | WO 2013/163210 A1 | 10/2013 |
| WO | WO 2014/009151 A1 | 1/2014 |
| WO | WO 2014/040088 A1 | 3/2014 |
| WO | WO 2014/076209 A1 | 5/2014 |
| WO | WO 2014/145899 A1 | 9/2014 |
| WO | WO 2014/160352 A1 | 10/2014 |
| WO | WO 2015/079042 A1 | 6/2015 |
| WO | WO 2015/083002 A2 | 6/2015 |
| WO | WO 2015/169933 A2 | 11/2015 |
| WO | WO 2015/189390 | 12/2015 |
| WO | WO 2016/033077 A1 | 3/2016 |

OTHER PUBLICATIONS

Baner, Johan et al., "Parallel Gene Analysis With Allele-Specific Padlock Probes and Tag Microarrays", Nucleic Acids Research, vol. 31, No. 17 (2003) pp. 1-7.
Baner, Johan et al., "Microarray-Based Molecular Detection of Foot-and-Mouth Disease, Vesicular Stomatitis and Swine Vesicular Disease Viruses, Using Padlock Probes", Journal of Virological Methods, 143 (2007) pp. 200-206.
Barisic, Ivan et al., "Multiplex Detection of Antibiotic Resistance Genes Using Padlock Probes", Diagnostic Microbiology and Infectious Disease, 77 (2013) pp. 118-125.
BD Diagnostics, "BD Phoenix, Automated Microbiology System" (2008) 13 pages.
BD Diagnostics, "BD Phoenix ID/AST Manual Panel Inoculation" (2012) 1 page.
BioMerieux SA, "Vitek 2 Instrument User Manual" (2008) 218 pages.
Birnboim, H. C. et al., "A Rapid Alkaline Extraction Procedure for Screening Recombinant Plasmid DNA", Nucleic Acids Research, vol. 7, No. 6 (1979) pp. 1513-1524.
Broeren, M. A. C. et al., "Antimicrobial Susceptibility Testing in 90 Min by Bacteria Cell Count Monitoring", Clinical Microbiology and Infection, vol. 19, No. 3 (2013) pp. 286-291.
Brown, Deborah A. et al., "Sorting of GPI-Anchored Proteins to Glycolipid-Enriched Membrane Subdomains During Transport to the Apical Cell Surface", Cell, vol. 68 (1992) pp. 533-544.
Chandler, Darrell P. et al., "Integrated Amplification Microarrays for Infectious Disease Diagnostics", Microarrays, 1 (2012) pp. 107-124.
Dahl, Fredrik et al., "Circle-To-Circle Amplification for Precise and Sensitive DNA Analysis", PNAS, vol. 101, No. 13 (2004) pp. 4548-4553.
De Jong, Ymke, "A Fast Antibiotic Susceptibility Test by Direct Staining", Uppsala Universitet, Thesis Report (2014) pp. 1-23.
Fire, Andrew et al., "Rolling Replication of Short DNA Circles", Proc. Natl. Acad. Sci. USA, vol. 92 (1995) pp. 4641-4645.
Fredborg, Marlene et al., "Real-Time Optical Antimicrobial Susceptibility Testing", Journal of Clinical Microbiology, vol. 51, No. 7 (2013) pp. 2047-2053.

GE Healthcare Lifesciences Handbook, "Nucleic Acid Sample Preparation for Downstream Analyses" (2013) 168 pages.
Gyarmati, Peter et al., "Simultaneous Genotyping of All Hemagglutinin and Neuraminidase Subtypes of Avian Influenza Viruses by Use of Padlock Probes", Journal of Clinical Microbiology, vol. 46, No. 5 (2008) pp. 1747-1751.
Handschur, M. Karlic et al., "Preanalytic Removal of Human DNA Eliminates False Signals in General 16S rDNA PCR Monitoring of Bacterial Pathogens in Blood", Comp. Immun. Microbiol. Infect. Dis., vol. 32 (2009) pp. 207-219.
Hardenbol, Paul et al., "Multiplexed Genotyping With Sequence-Tagged Molecular Inversion Probes", Nature Biotechnology, vol. 21, No. 6 (2003) pp. 673-678.
Harrison, Susan T. L., "Bacterial Cell Disruption: A Key Unit Operation in the Recovery of Intracellular Products", Biotech. Adv., vol. 9 (1991) pp. 217-240.
Ishii, Reina et al., "Counting Single DNA Molecule by On-Bead Rolling Circle Amplification for Quantitative Analyses", $15^{th}$ International Conference on Miniaturized Systems for Chemistry and Life Sciences (2011) pp. 70-72.
Jarvius, Jonas et al., "Digital Quantification Using Amplified Single-Molecule Detection", Nature Methods, vol. 3, No. 9 (2006) pp. 725-727 (with Supplementary note—16 pages).
Kagan, Robert L. et al., "Rapid Automated Diagnosis of Bacteremia by Impedance Detection", Journal of Clinical Microbiology, vol. 5, No. 1 (1977) pp. 51-57.
Ke, Rongqin et al., "Colorimetric Nucleic Acid Testing Assay for RNA Virus Detection Based on Circle-to-Circle Amplification of Padlock Probes", Journal of Clinical Microbiology, vol. 49, No. 12 (2011) pp. 4279-4285.
Kesberg, Anna Isabella et al., "Improved Protocol for Recovery of Bacterial DNA From Water Filters: Sonication and Backflushing of Commercial Syringe Filters", Journal of Microbiological Methods, 93, 2 (2013) pp. 1-7.
Koltai, Hinanit et al., "Survey and Summary—Specificity of DNA Microarray Hybridization: Characterization, Effectors and Approaches for Data Correction", Nucleic Acids Research, vol. 36, No. 7 (2008) pp. 2395-2405.
Kumar MD, Anand et al., "Duration of Hypotension Before Initiation of Effective Antimicrobial Therapy Is the Critical Determinant of Survival in Human Septic Shock", Critical Care Medicine, vol. 34, No. 6 (2006) pp. 1589-1596.
Lahanas, Sophie et al., "Evaluation of the Alfred 60/AST as a Screening Test for Urinary Tract Infections", Journal of Clinical Microbiology (2013) pp. 1-13.
Landegren, Ulf et al., "A Ligase-Mediated Gene Detection Technique", Science, vol. 241 (1988) pp. 1077-1080.
Larsson, Chatarina et al., "In Situ Genotyping Individual DNA Molecules by Target-Primed Rolling-Circle Amplification of Padlock Probes", Nature Methods, vol. 1, No. 3 (2004) pp. 227-232.
Liesenfeld, O. et al., "Molecular Diagnosis of Sepsis: New Aspects and Recent Developments", European Journal of Microbiology and Immunology, 4, 1 (2014) pp. 1-25.
Liu, Quanjun et al., "Microarray-in-a-Tube for Detection of Multiple Viruses", Clinical Chemistry, 53:2 (2007) pp. 188-194.
Lizardi, Paul M. et al., "Mutation Detection and Single-Molecule Counting Using Isothermal Rolling-Circle Amplification", Nature Genetics, vol. 19 (1998) pp. 225-232.
Loonen, Anne J. M. et al. "Comparison of Pathogen DNA Isolation Methods From Large Volumes of Whole Blood to Improve Molecular Diagnosis of Bloodstream Infections", PLOS ONE, vol. 8, Issue 8 (2013) pp. 1-7.
Lorenz, Michael, "SelectNA Plus—Walk-Away Automated Extraction of Microbial DNA From Clinical Samples", Molzym GmbH & Co. KG, Molzym's Tapas Symposium Direct Molecular Testing (2014) pp. 1-6.
Metzger, S. et al., "Direct Identification of Methicillin Resistant *Staphylococcus aureus* (MRSA) Using Small Numbers of Immobilized Cells and Response to Oxacillin (OXA) by Automated Growth Analysis", ASM, Accelr8 Technology Corporation (2007), 1 page.

(56) References Cited

OTHER PUBLICATIONS

Metzger, S. et al., "Rapid Identification of Resistance Phenotypes in Gram-Negative Bacilli Using Automated Digital Microscopy", ASM, Accelr8 Technology Corporation (2009), 1 page.
Metzger, S. et al., "Same-Day ID and Resistance Phenotyping Directly From Respiratory Specimens by Automated Microscopy", ASM, Accelr8 Technology Corporation (2011), 1 page.
Metzger, S. et al., "Rapid Simultaneous Identification and Quantitation of *Staphylococcus aureus* and Pseudomonas Aeruginosa Directly From Bronchoalveolar Lavage Specimens Using Automated Microscopy", Diagnostic Microbiology and Infectious Disease, 79 (2014) pp. 160-165.
Mothershed, Elizabeth A. et al., "Nucleic Acid-Based Methods for the Detection of Bacterial Pathogens: Present and Future Considerations for the Clinical Laboratory", Clinica Chimica Acta, 363 (2006) pp. 206-220.
Nilsson, Mats et al., "Padlock Probes: Circularizing Oligonucleotides for Localized DNA Detection", Science, vol. 265 (1994) pp. 2085-2088.
Prere, M.-F. et al., "Rapid Identification of Bacteria, mecA and Van Genes From Blood Cultures", Pathologie Biologie 55 (2007) pp. 375-377.
Rajagopal, Soumitra et al., "Eight Gram-Negative Bacteria Are 10 000 Times More Sensitive to Cationic Detergents Than to Anionic Detergents", Can. J. Microbiol. 49 (2003) pp. 775-779.
Sage, Jr., Burton H. et al., "Rapid Visual Detection of Microorganisms in Blood Culture", Journal of Clinical Microbiology, vol. 20, No. 1 (1984) pp. 5-8.
Sartor, Maureen et al., "Microarray Results Improve Significantly as Hybridization Approaches Equilibrium", BioTechniques, vol. 36, No. 5 (2004) pp. 790-796.
Sato, Kae et al., "Microbead-Based Rolling Circle Amplification in a Microchip for Sensitive DNA Detection", The Royal Society of Chemistry, Lab Chip, vol. 10 (2010) pp. 1262-1266.
Schweitzer, Barry et al., "Multiplexed Protein Profiling on Microarrays by Rolling-Circle Amplification", Nat Biotechnol., 20, 4 (2002) pp. 1-17.
Siemens, "MicroScan Dried Conventional Gram Negative Panels", Siemens Healthcare Diagnostics (2012) 4 pages.
Smith, James H. et al., "Detection of Nucleic Acid Targets Using Ramified Rolling Circle DNA Amplification: A Single Nucleotide Polymorphism Assay Model", PLOS ONE, vol. 8, Issue 5 (2013) pp. 1-8.
Spezzotti, Gianpiero, "Technical Notes on the Correct Configuration of the Alfred 60/AST Device for the Detection of Urinary Tract Infections", Journal of Clinical Microbiology, vol. 52, No. 5 (2014) pp. 1805-1806.
Sullivan, Nadine M. et al., "Practical Aerobic Membrane Filtration Blood Culture Technique: Development of Procedure", Journal of Clinical Microbiology, vol. 1, No. 1 (1975) pp. 30-36.
Sullivan, Nadine M. et al., "Practical Aerobic Membrane Filtration Blood Culture Technique: Clinical Blood Culture Trial", Journal of Clinical Microbiology, vol. 1, No. 1 (1975) pp. 37-43.
Tenover, Fred C. et al., "Vancomycin-Resistant *Staphylococcus aureus* Isolate From a Patient in Pennsylvania", Antimicrobial Agents and Chemotherapy, vol. 8, No. 1 (2004) pp. 275-280.
Torio, Celeste M. et al., "National Inpatient Hospital Costs: The Most Expensive Conditions by Payer, 2011", Agency for Healthcare Research and Quality, Rockville, MD, HCUP Statistical Brief #160 (2013) 12 pages.
Van Belkum, Alex, et al., "Next-Generation Antimicrobial Susceptibility Testing", Journal of Clinical Microbiology, vol. 51, No. 7 (2013) pp. 2018-2024.
Wei, Cheng-Wey et al., "Using a Microfluidic Device for 1 μl DNA Microarray Hybridization in 500 s", Nucleic Acids Research, vol. 33, No. 8 (2005) pp. 1-11.
Whittier, S. et al., "Evaluation of the BD Phoenix Automated Microbiology System for Antibiotic Susceptibility Testing of *Streptococcus pneumoniae*", American Society for Microbiology 106th General Meeting (2006) 4 pages.

Wiles, T. et al., "Rapid Antimicrobial Susceptibility Testing in Phoenix", American Society for Microbiology 99th General Meeting (1999) 3 pages.
Wu, S.-J. et al., "Preparation of Milk Samples for PCR Analysis Using a Rapid Filtration Technique", Journal of Applied Microbiology, 96 (2004) pp. 1342-1346.
Zierdt, Charles H. et al., "Development of a Lysis-Filtration Blood Culture Technique", Journal of Clinical Microbiology, vol. 5, No. 1 (1977) pp. 46-50.
Zierdt, Charles H., "Blood Lysing Solution Nontoxic to Pathogenic Bacteria", Journal of Clinical Microbiology, vol. 15, No. 1 (1982) pp. 172-174.
Zierdt, Charles H. et al., "Lysis-Filtration Blood Culture Versus Conventional Blood Culture in a Bacteremic Rabbit Model", Journal of Clinical Microbiology, vol. 15, No. 1 (1982) pp. 74-77.
Zierdt, Charles H., "Simplified Lysed-Blood Culture Technique", Journal of Clinical Microbiology, vol. 23, No. 3 (1986) pp. 452-455.
BD Phoenix, Laboratory Procedure, (Date), pp. 1-30, at least as early as Jun. 13, 2014.
Mezger, MSc, Anja et al., "Rapid Antibiotic Susceptibility Testing for Urinary Tract Infections", Uppsala Universitet, Science for Life Laboratory, (Date), 1 page, at least as early as Jun. 13, 2014.
Pezzlo, M. T. et al., "High Recovery of Bacteria and Fungi in Low Concentrations From Liquid Samples", Pocared Diagnostics 2064, (Date), 7 pages, at least as early as Jun. 13, 2014.
Broeren et al., "Antimicrobial Susceptibility Testing in 90 Min by Bacterial Cell Count Monitoring", Clinical Microbiology and Infection, vol. 19, No. 3, (2013), pp. 286-291.
Göransson et al., "Rapid Identification of Bio-Molecules Applied for Detection of Biosecurity Agents Using Rolling Circle Amplification", Plos One, vol. 7, No. 2, (2012), pp. 1-9.
Jorgensen et al., "Antimicrobial Susceptibility Testing: A Review of General Principles and Contemporary Practices", Clinical Infectious Diseases, vol. 49, No. 11, (2009), pp. 1749-1755.
Liesenfeld et al., "Molecular Diagnosis of Sepsis: New Aspects and Recent Developments", European Journal of Microbiology and Immunology, vol. 4 (2014) 1, pp. 1-25.
Metzger et al., "Rapid Simultaneous Identification and Quantitation of *Staphylococcus aureus* and Pseudomonas Aeruginosa Directly From Bronchoalveolar Lavage Specimens Using Automated Microscopy", Diagnostic Microbiology and Infectious Disease, 79, (2014), pp. 160-165.
Mothershed et al., "Nucleic Acid-Based Methods for the Detection of Bacterial Pathogens: Present and Future Considerations for the Clinical Laboratory", Clinica Chimica Acta, vol. 363, No. 1-2, (2006), pp. 206-220.
Price et al., "Rapid Antibiotic Susceptibility Phenotypic Characterization of *Staphylococcus aureus* Using Automated Microscopy of Small Numbers of Cells", Journal of Microbiological Methods, 98 (2014) pp. 50-58.
International Search Report and Written Opinion of International Application No. PCT/EP2015/063173 dated Jul. 20, 2015, 11 pages.
International Search Report and Written Opinion of International Application No. PCT/EP2016/058952 dated Aug. 24, 2016, 11 pages.
International Search Report and Written Opinion of International Application No. PCT/EP2017/059542 dated Jul. 17, 2017, 13 pages.
U.K. Search Report of British Application No. GB1507026.1 dated Oct. 27, 2014, 4 pages.
U.K. Search Report of British Application No. GB1606991.6 dated Jan. 26, 2017, 4 pages.
U.K. Search Report of British Application No. GB1617353.6 dated Jan. 31, 2018, 7 pages.
Brooks, Mark et al., "Policy for the Transport of Pathology Samples", Pathology—Transport of Pathology Samples GP/MP6, Version 3.4, Aug. 2014, pp. 1-11.
Olson, Walter C. et al., "Shipping Blood to a Central Laboratory in Multicenter Clinical Trials: Effect of Ambient Temperature on Specimen Temperature, and Effects of Temperature on Mononuclear Cell Yield, Viability and Immunologic Function", Journal of Translation Medicine, 2011, 9:26 (https://www.ncbi.nlm.nih.gov/pmc/articles/PMC3063218/pdf/1479-5876-9-26.pdf).

(56) References Cited

OTHER PUBLICATIONS

Giacomazzi, C. G., et al, "Rapid diagnosis of tuberculosis and multidrug resistance with the microscopic observation drug susceptibility assay in Ecuador." Int. J. Tuberc. Lung Dis., vol. 14, No. 6, pp. 786-788 (2010).

* cited by examiner

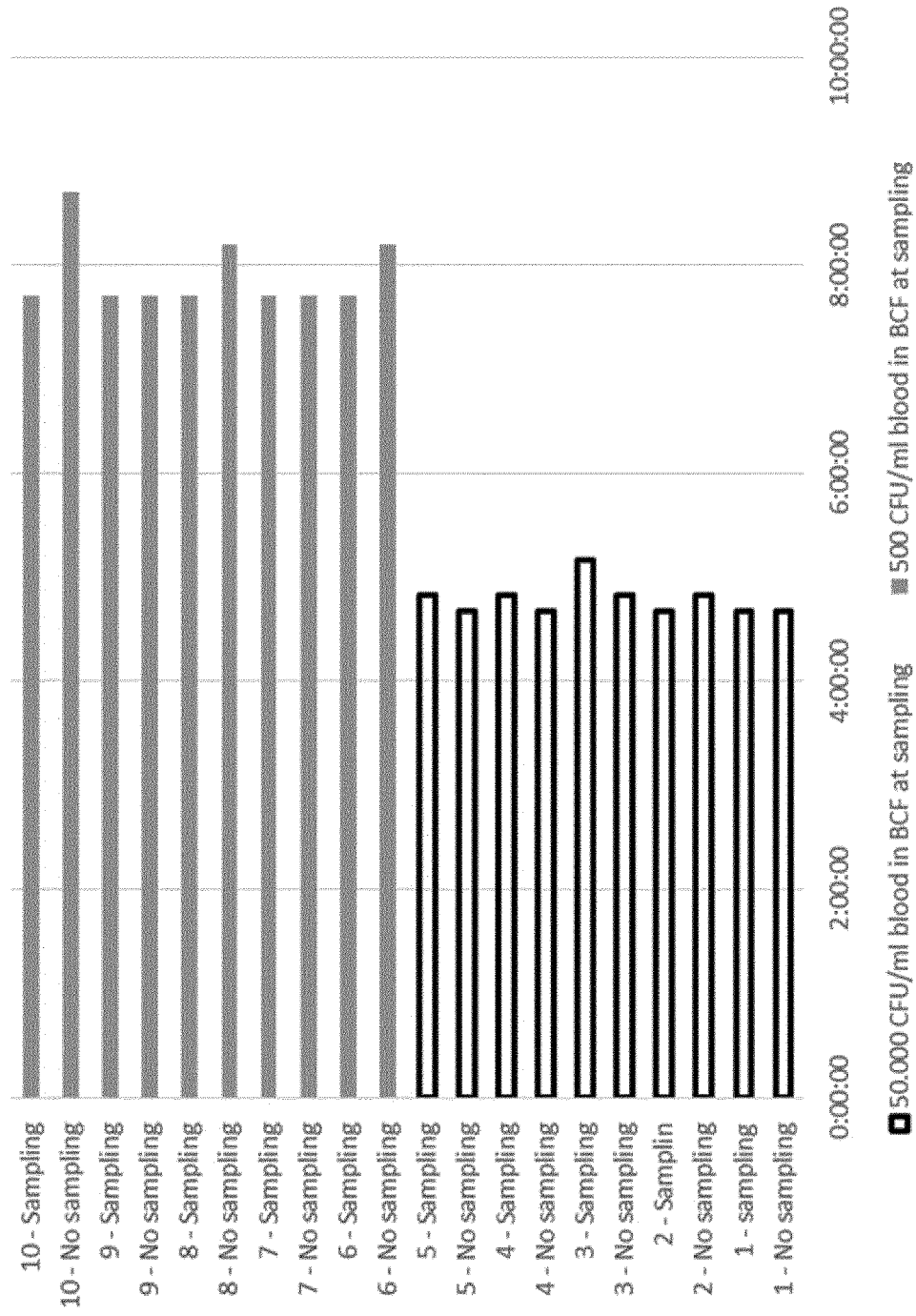

METHOD FOR DETERMINING THE IDENTITY AND ANTIMICROBIAL SUSCEPTIBILITY OF A MICROORGANISM

The present invention relates to a method for detecting and characterising a microorganism in a clinical sample. In particular the present invention provides a rapid molecular testing method for the combined detection and characterisation of a microorganism that allows the continued culturing of a sample for further testing.

Microbial infections represent a major class of human and animal disease with significant clinical and economic implications. Whilst various classes and types of antimicrobial agents are available to treat and/or prevent microbial infections, antimicrobial resistance is a large and growing problem in modern medicine. The numbers of antimicrobial-resistant strains of various microbial pathogens have proliferated in the past 20 years, and microorganisms continue to develop resistance to a growing number of antimicrobial, particularly antibiotic, classes. With the spread of resistance mechanisms to more organisms, the public health impact and costs associated with antimicrobial resistance are projected to increase rapidly in the years to come. In the context of treatment of a microbial infection, it can therefore be desirable, and indeed important, to have information regarding the nature of the infecting microorganism and its antimicrobial susceptibility profile in order both to ensure effective treatment and also to reduce the use of unnecessary or ineffective antibiotics and thereby to help control the spread of antibiotic, or more generally antimicrobial, resistance. This is particularly so in the case of serious or life-threatening infections in which rapid effective treatment is vital.

Sepsis, a potentially fatal whole-body inflammation caused by severe infection is the most expensive condition and driver of hospital costs in the US, comprising 5% of the total national hospital cost. Mortality increases 7% for every hour for severe sepsis, if not treated properly, and the rising prevalence of antimicrobial-resistant sepsis causing strains makes predictions of the correct treatment for sepsis increasingly difficult. The current gold standard for diagnosis of the microorganisms causing sepsis is based on phenotypic and biochemical identification techniques which require the isolation and culture of pure cultures of the infecting microorganisms. It can take several days to perform the microbial identification (ID) and antibiotic susceptibility (AST) tests to identify the infection and determine the susceptibility profile of antimicrobial resistant microorganisms. Current clinical practice requires treatment with a broad-spectrum antibiotic within 1 hour of suspicion of sepsis based on clinical symptoms. A second dose is required within 6-8 hours and this administration is continued every sixth to eighth hour until identification of the microorganism and its antibiotic susceptibility (ID/AST) is established.

Due to the lethal condition of sepsis physicians are unwilling to change treatment from broad-spectrum antibiotics initially if the patient experiences a clinical response until the nature of the microbial infection is determined and antimicrobial susceptibility established. This in turn leads to the unnecessarily high use of broad spectrum antibiotics, in turn fuelling the rise of antimicrobial resistance among microorganisms.

Conventional testing methods utilise turbidity measurements or disc diffusion to assess the effect of antimicrobial agents on microorganism growth, and traditional biochemical and microbiological techniques to identify a microorganism. These techniques can take several days to identify and characterise a microorganism in a clinical sample, due to the requirement for prolonged periods of incubation to allow microbial growth. There is thus a requirement for techniques can rapidly identify microorganisms and determine the antimicrobial susceptibility profile of antimicrobial resistant microorganisms, and various different techniques that reduce the time between sample collection and diagnosis have been developed in recent years.

Methods of enriching microorganisms in a clinical sample that bypass the requirement for long periods of incubation are described in U.S. Pat. No. 8,481,265; microbial cells can be enriched from clinical samples by the selective lysis of non-microbial cells, enriching the concentration of microbial cells in a sample and bypassing the requirement for prolonged incubation prior to testing a sample.

Methods of rapid microbial identification are described in US 2010/0124763, in which microbial cultures are enriched and microorganisms identified spectroscopically.

Rapid susceptibility testing techniques using flow cytometry (Broeren et al. 2013 Clin Microbiol Infect 19, 286-291) and automated microscopy (Price et al. 2014 JMM. 98 50-59) have been developed to reduce the time required for incubation prior to susceptibility being determined. Quantitative PCR of microbial DNA has also been used as a measure for microbial growth to determine antimicrobial susceptibility, as described in U.S. Pat. No. 5,789,173.

Combined microorganism identification and susceptibility testing methods have also been developed. Described in US 2005/0095665 A1 is a system in which panels of selected growth media and chromogenic and fluorogenic substrates are used in combination with turbimetric measurement of microbial growth in an automated microtititer well format to identify microorganisms and determine antimicrobial susceptibility. Automated microscopy methods have also been developed (Metzger et al. 2014 Diagnostic Microbiology and Infectious Disease 79 160-165). The BD Phoenix™ system also allows for the rapid simultaneous identification and characterisation of microorganisms, and utilises a variety of chromogenic and fluorogenic substrates to identify microorganisms in a sample and minor microbial growth to determine the antimicrobial susceptibility of microorganisms in a sample.

Molecular methods for microbial identification have been developed in which, rather than growing and testing the properties of the microorganisms, probes are used to detect nucleic acid or protein markers in or on the microbial cells, which markers can identify the microorganism. A number of such molecular tests for identifying different microorganisms have been developed, and indeed molecular tests also exist for identifying various genetic variants, or genetic signatures, associated with resistance markers to particular antimicrobial agents.

However, despite the development of such new techniques for the identification and characterisation of microorganisms, clinicians remain cautious about relying solely on their use over traditional culture and phenotypic/biochemical methods, and such traditional methods remain a mainstay in many clinical laboratories today. In particular as regards molecular tests, due to a perception that the probes available may not detect all possible potential pathogens (and therefore a perceived lack of "completeness" of molecular tests), many clinicians are reluctant to rely solely on these and regard them only as a complementary test. Thus current clinical practice is to supplement traditional culture methods with molecular testing methods to diagnose infectious diseases. Whilst these traditional methods also lack completeness, their established use makes them the current gold standard for diagnosing infectious diseases.

Current clinical practice therefore requires the collection of duplicate clinical samples from a patient in order that both molecular and traditional tests can be performed in parallel. This can lead to logistical and personnel issues as additional staff are required to collect and handle samples, and can lead to unacceptable delays in the diagnosis and treatment of an infectious disease in a patient. This also carries the risk that additional false-positive diagnoses due the high risk of contamination from the taking of a clinical sample. This can lead in some cases to molecular tests being foregone, despite the fact that they could potentially lead to an earlier identification and diagnosis.

The present invention seeks to address these problems, and in particular to provide an improved workflow which accommodates both molecular and traditional testing methods using the same clinical sample. The present invention thus provides a method for detecting and characterising a microorganism in a clinical sample in which the same clinical sample is available for molecular testing and a rapid antimicrobial susceptibility test (AST), and for traditional culture methods, which eliminates the need for duplicate clinical samples to be taken. Indeed, the method is designed such that whilst the sample is cultured to allow the growth of microorganisms during the time that molecular tests are taking place, if the molecular tests lead to an identification, the performance of traditional or conventional tests may not be necessary—the molecular ID and resistance tests coupled with the rapid AST tests may be sufficient, thereby obviating the need for any further, conventional or traditional, culture-based tests. Nonetheless, the method allows for the same sample to be kept in culture in case such tests are required, or indeed to allow such additional tests to be performed in any event, as a confirmation or back-up of the results. This leads to faster diagnosis than conventional methods, and can lead to the faster treatment of patients as well as faster out-phasing of un-necessary treatment. If molecular testing is not sufficient to identify the microorganism, then further conventional tests can be performed using the same sample. This elegant solution to the problem has not previously been appreciated or proposed.

A key feature of the present invention is that a single sample is taken from the patient—this single sample may be placed into and kept in culture while the molecular tests and AST according to the invention is performed. However, it is not essential that only a single culture is prepared and incubated (cultured). It is possible that a single initial culture may be set up (e.g. a single culture vessel may be inoculated with the clinical sample) and from this one or more sub-cultures may be set up, and a sub-culture of the initial culture may be used for the molecular and AST tests according to the invention. The initial primary culture may be maintained (i.e. maintained in culture) in case further tests are necessary or desirable.

Accordingly, in one aspect the present invention provides a method for detecting and characterising a microorganism in a clinical sample, in particular a microorganism that may be present in a clinical sample, said method comprising:

a) introducing a clinical sample to a first culture vessel containing culture medium;

b (i)) optionally preculturing said clinical sample in said first culture vessel;

b (ii) optionally removing a portion of the clinical sample/medium mixture or, if precultured, the clinical sample culture from said first culture vessel, and introducing said portion to a second culture vessel containing culture medium, and optionally preculturing said portion in said second culture vessel;

c) removing a test aliquot from said first and/or second culture vessel, and culturing or continuing to culture said clinical sample and/or portion in said first and/or second culture vessel;

d) separating DNA from said test aliquot;

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, a said probe or primer being capable of hybridising specifically to, or a said primer being capable of selectively amplifying, a nucleotide sequence which is identificatory of a given microorganism; and ii) one or more nucleic acid probes and/or primers for antimicrobial resistance marker detection, a said probe or primer being capable of hybridising specifically to, or a said primer being capable of selectively amplifying, a nucleotide sequence representing a genetic antimicrobial resistance marker;

and it is detected whether or not said probes and/or primers have hybridised to said DNA and/or said primers have been extended (e.g. an amplification reaction has taken place); and f) if a microorganism is identified in step (e), performing an antimicrobial susceptibility test on said cultured clinical sample and/or portion from step (c), wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in step (e), and optionally continuing to culture said clinical sample and/or portion in said first and/or second culture vessel or g) if no microorganism strain is identified in step (e), further culturing said clinical sample and/or portion to enable further microbial identification and antimicrobial susceptibility tests to be performed to identify the microorganism and determine its antimicrobial resistance profile.

It will be seen that the method of the invention relies upon setting up a culture of the clinical sample which ultimately would enable conventional culture-based identification and susceptibility tests to be performed, whilst at the same time removing aliquots (or portions) of the culture to enable firstly molecular tests, and secondly a rapid AST, to be performed which may advantageously obviate the need for the conventional tests. The method thus allows molecular tests to be performed whilst preserving the option of using the same clinical sample for further conventional tests, by culturing it while the molecular tests (step (e)), and optionally also the AST of step (f), are performed. This can be a single culture (e.g. continuing to incubate the clinical sample) or a further culture may be set up e.g. which may be used to provide an aliquot for testing whilst the first or initial culture is maintained in culture (i.e. continues to be cultured). Indeed by continuing to culture the sample or portion during the molecular tests of step (e), and optionally also during step (f), the culturing required for the further (e.g. conventional) tests is in effect being performed in parallel with the molecular and AST tests of steps (e) and (f). Accordingly, step (f) of the method may in certain embodiments be expressed as performing an antimicrobial susceptibility test on a further aliquot of the cultured clinical sample or portion from step (c).

Whilst setting up and maintaining a single initial (i.e. "first") culture may be provide a simple and convenient workflow, using a single culture system, at least until such time as a negative or inconclusive result is obtained from the molecular tests, it may in some cases be desirable to have the flexibility to use different culture systems, which can be achieved by setting up a sub-culture (e.g. second culture) of the initial first culture. As will be explained in more detail below, for example once a second culture is set up, the first culture can be moved to a different culture system, e.g. to a conventional culture cabinet, and the second culture can be cultured (or more particularly maintained or continued) in a dedicated culture system (e.g. instrument) for the molecular and rapid AST tests of the present invention.

Thus, in one particular aspect the method of the present invention comprises:

a) introducing a clinical sample to a culture vessel containing culture medium;

b) optionally preculturing said clinical sample in said culture vessel;

c) removing a test aliquot from said culture vessel, and culturing or continuing to culture said clinical sample in said culture vessel;

d) separating DNA from said test aliquot;

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, a said probe or primer being capable of hybridising specifically to, or a said primer being capable of selectively amplifying, a nucleotide sequence which is identificatory of a given microorganism; and ii) one or more nucleic acid probes and/or primers for antimicrobial resistance marker detection, a said probe or primer being capable of hybridising specifically to, or a said primer being capable of selectively amplifying, a nucleotide sequence representing a genetic antimicrobial resistance marker;

and it is detected whether or not said probes and/or primers have hybridised to said DNA and/or said primers have been extended (e.g. an amplification reaction has taken place); and f) if a microorganism is identified in step (e), performing an antimicrobial susceptibility test on said cultured clinical sample from step (c), wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in step (e), and optionally continuing to culture said clinical sample in said culture vessel; or g) if no microorganism strain is identified in step (e), further culturing said clinical sample to enable further microbial identification and antimicrobial susceptibility tests to be performed to identify the microorganism and determine its antimicrobial resistance profile.

As noted above, in a further aspect a further culture may be set up from the clinical sample. In one such embodiment a clinical sample may be introduced into a first culture vessel containing culture medium, and either immediately or after an optional period of preculturing a portion of the content of the first culture vessel (i.e. either of the clinical sample/culture medium mixture or of a culture of the clinical sample in the first culture vessel) may be removed and used to inoculate a second culture vessel. As mentioned above and explained further below a dedicated instrument or device may be provided to perform the method of the invention, and this may be used alongside a conventional culture system or instrument for performing conventional tests if desired or necessary (e.g. a culture cabinet from Becton Dickinson or Biomerieux). Such a dedicated instrument/device may be designed to receive a first culture vessel containing the clinical sample, and to remove a portion from the first culture vessel and introduce it into the second culture vessel. This may allow the first culture vessel containing the clinical sample and the culture medium (e.g. a blood culture flask) to be placed in a further culture system (e.g. incubator) for testing via conventional means, whilst the portion of the clinical sample/culture medium mixture or clinical sample culture obtained therefrom is retained in the device of the present invention for culturing (including optional preculturing) and AST and ID testing.

The method of the present invention may therefore comprise:

a) introducing a clinical sample to a first culture vessel containing culture medium;

b(i) optionally preculturing said clinical sample in said first culture vessel;

b(ii)) removing a portion of the clinical sample/culture medium mixture, or, if precultured, of the clinical sample culture from said first culture vessel, and introducing said portion to a second culture vessel containing culture medium and optionally preculturing said portion in said second culture vessel;

c) removing a test aliquot from said second culture vessel, and culturing or continuing to culture said portion in said second culture vessel;

d) separating DNA from said test aliquot;

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, a said probe or primer being capable of hybridising specifically to, or a said primer being capable of selectively amplifying, a nucleotide sequence which is identificatory of a given microorganism; and ii) one or more nucleic acid probes and/or primers for antimicrobial resistance marker detection, a said probe or primer being capable of hybridising specifically to, or a said primer being capable of selectively amplifying, a nucleotide sequence representing a genetic antimicrobial resistance marker;

and it is detected whether or not said probes and/or primers have hybridised to said DNA and/or said primers have been extended (e.g. an amplification reaction has taken place); and f) if a microorganism is identified in step (e), performing an antimicrobial susceptibility test on said cultured portion from step (c), wherein microbial growth in said antimicrobial susceptibility test is monitored by assessing growth or markers for growth, and wherein the type and concentration of antimicrobial agents used in said antimicrobial susceptibility test is determined by the identity of the microorganism and antimicrobial resistance markers detected in step (e), and optionally continuing to culture said portion in said second culture vessel or g) if no microorganism strain is identified in step (e), further culturing said clinical sample and/or portion to enable further microbial identification and antimicrobial susceptibility tests to be performed to identify the microorganism and determine its antimicrobial resistance profile.

Indeed, in any of the embodiments of the present invention further ID and/or AST tests, whether conventional or not, may be performed on the cultured sample or portion irrespective of whether or not a positive identification result in step (e) is obtained. The method therefore allows for culture of the clinical sample or portion to take place to allow additional identification and/or AST tests to be performed, for example simply to provide an additional result, e.g. as a back-up or confirmation. In a further embodiment, further (e.g. conventional) tests may be performed whether or not there is a positive result from the ID tests of step (e) and/or the AST test of step (f). In a preferred aspect, culturing of the clinical sample (i.e. of the first culture vessel) is continued to enable further microbial identification and antimicrobial susceptibility tests to be performed It will further be understood that the tests of steps (e) and/or (f) may be repeated, or performed one or more times, that is to say aliquots may be removed from the first or second culture one or more times, e.g. at intervals, to perform the nucleic acid tests of step (f) one or more times (e.g. two or more times, e.g. 2 or 3 times). Optionally, the AST test of step (f) may also be performed more than once, should this be desired. As noted above, culture of the clinical sample in the culture vessel may be continued, whilst the AST test of step (f) is going, and optionally also after the test has been performed. Thus the possibility exists of repeating the AST test or of continuing the culture to allow conventional testing. As is clear from the context, an aliquot of the clinical sample/culture medium mixture or portion removed therefrom in the first or second culture vessel is simply a portion, i.e. a part or fraction of the culture vessel contents. The aliquot may be removed and used directly for the nucleic acid tests of step (e), (that is after separating DNA from the test aliquot in step (d)), or in an AST test of step (f), or it may be subjected to a period of culture before performing the tests of steps (d)/(e) and/or step (f). Further, a test aliquot removed from the first or second culture vessel may be divided into sub-aliquots or aliquot fractions, or a sub-aliquot or fraction may be removed therefrom, which may be subjected to testing or further culture. This culture of a removed test aliquot or aliquot fraction may be performed separately, or independently, of the culture or continued culture of the clinical sample in the culture vessel.

The step of culturing the clinical sample in the culture vessel or of the portion removed from the first culture vessel, or indeed of culturing a test aliquot/aliquot fraction, may be performed in any convenient or desired way, as described in more detail below. In this regard, culture apparatus for culture of clinical samples for e.g. diagnostic or microbial detection purposes are known and may be used. Different culture apparatus or culture systems may be used for the separate culture of the culture vessel (e.g. the first and second culture vessels), and/or of any removed test aliquots/aliquot fractions and/or for the culture required during the AST test. Furthermore, as mentioned above and described in more detail below, it is envisaged according to the present invention also to provide an apparatus, or device, for performing the microbial detection and characterisation method as described herein. Such a device, or system, may include apparatus or means for culturing the culture vessel. Accordingly the various culture steps of the method, including the culture/continued culture of the first and/or second culture vessel, the optional preculture of the first and/or second culture vessel prior to removing a test aliquot (e.g. the first test aliquot), the culture of a test aliquot or aliquot fraction, or indeed also culture during the AST test of step (f) may be performed in the same or different culture systems or culture apparatus. The culture vessel may be transferred to a different culture system/apparatus, for example if there is a negative result from the identification test of step (e). The surface of a culture vessel (e.g. a first and/or second culture vessel) may be cleaned or decontaminated prior to being placed in a culture apparatus (e.g. after the clinical sample or portion has been introduced into the culture vessel).

Thus for example, in one embodiment, the culture vessel (e.g. a first culture vessel) may be cultured in one system whilst the optional preculture, and the testing steps are being performed. If the identification tests of step (e) are negative and/or inconclusive, or if the AST test of step (f) is negative, inconclusive or incomplete, the culture vessel may then be transferred to a further, or separate culture system, e.g. to enable conventional identification tests and/or AST tests to be performed. For example, such a further or separate culture system may be a conventional culture cabinet, or a further automated microbial testing/detection system (e.g. diagnostic system).

By way of representative example, in one embodiment of the method, the clinical sample, collected from a test subject is introduced into a culture vessel (this can be regarded as a first culture vessel) (step (a)). Before any culture takes place, a test aliquot is removed (step (c)), and subjected to steps (d) and (e). During this time the culture vessel is cultured. If the identification test of step (e) yields a positive result, a further aliquot is removed from the culture vessel and subjected to the AST of step (f). If the identification test in step (e) is negative, the culture vessel containing the clinical sample is subjected to further culturing, e.g. in a separate system.

In a second embodiment, the method is performed as described above, but with a step of preculture before removing a test aliquot in step (c).

In a third embodiment, a test aliquot is removed from the culture vessel (step (c) as above), and from this aliquot a fraction is subjected to steps (d) and (e) (nucleic acid separation and detection). During this time a further aliquot fraction or the remainder of the test aliquot is subjected to culture, as is the culture vessel from which the test aliquot is removed. This culture of the separate aliquot/aliquot fraction and culture vessel may take place in the same or different systems. If the identification test of step (e) yields a positive result, the cultured further aliquot fraction/remaining aliquot is subjected to the AST of step (f). If the identification test in step (e) is negative, the culture vessel containing the clinical sample is subjected to further culturing, e.g. in a separate system.

In a fourth embodiment, a portion is removed from the first culture vessel (whether before or after a period of preculture) and introduced into a second culture vessel containing culture medium. A test aliquot is removed from the second culture vessel (step (c), and subjected to steps (d) and (e). During this time the second culture vessel is cultured. If the identification test of step (e) yields a positive result, a further aliquot is removed from the second culture vessel and subjected to the AST of step (f). If the identification test in step (e) is negative, the second culture vessel containing the sample aliquot is subjected to further culturing. In a further embodiment, the first culture vessel may additionally or instead be subjected to further culturing, e.g. in a separate system.

In a further embodiment, the first, second, third and/or fourth representative embodiments described above may include continued culture of the culture vessel containing the clinical sample irrespective of whether a positive or negative identification result in step (e) was obtained. In this way an additional result may be obtained from the sample.

It will be seen therefore that in certain preferred embodiments molecular testing takes place (i.e. the nucleic acid tests of step (e)) without any culture of the clinical sample. In many microbial testing procedures as carried out today, identification tests (whether by conventional biochemical tests or by molecular tests) take place once there has been a positive result in a microbial culture, namely once microbial growth has been detected (a positive culture test). Thus for example, a blood or other sample is introduced to a culture vessel (e.g. a blood culture flask), and this is cultured. The culture system is designed or selected to indicate that (when) microbial growth has occurred, for example by including an indicator substance that yields a signal dependent on microbial growth (e.g. due to pH change, or conversion/consumption of a substrate, or generation of microbial metabolic product etc.) or simply by detecting microbial growth by any means. When/if sufficient microbial growth occurs to yield a signal/give detectable growth, this indicates a "positive" result in the culture/microbial detection (i.e. that there is growth of a microorganism in the clinical sample, although it is not known at this stage what is the identity of the microorganism). At this stage the identification and/or AST tests are usually performed. The microbial growth test may take some hours e.g. 6, 8, 10 or 12 hours or more, to perform.

The present invention has the advantage that it is not necessary to wait until a positive result in such a culture test has been obtained, meaning that a microbial identification may be more rapidly obtained. Step (b) allows for an optional preculture step before molecular testing. This may be for a period which is shorter than necessary for a positive culture test. Thus in one representative embodiment, steps (d) and (e) take place before there is a positive culture test result. In a further embodiment, steps (d) and (e) are first performed before a positive culture result is obtained (or before the time that would be required to obtain a positive culture result) and may be repeated after a positive culture result (or the time period required for a positive result). In other words, in one preferred embodiment at least one set of nucleic acid tests (step (e)) is performed before there is a positive culture result, or more particularly before the time that would be required for a positive culture result to be obtained. In a further representative embodiment, step (f) (an AST step) may also be performed before a positive result is obtained or obtainable in a culture test. However, it is not precluded according to the method of the present invention to perform the testing steps (e) and (f) after a positive culture result, e.g. to remove the test aliquot in step (c) after a positive test result. In such a case it can be seen that a preculture step (b) may involve culturing the culture vessel until a positive culture test result is obtained or until such time as a positive culture test result would be expected.

In relation to the nucleic acid tests of step (e) in one preferred embodiment a first set of nucleic acid probes are used which hybridise specifically to a nucleic sequence which is identificatory of a microorganism and a second set of probes which hybridise specifically to a nucleotide sequence which represents a genetic antimicrobial resistance marker. In such an embodiment detection of probe hybridisation may involve, or may take place by, probe amplification. Thus detection of probe hybridisation may be performed by detecting probe amplification. Accordingly the method of the invention may in step (e) comprise the use of one or more amplification primers for the probe, that is primer(s) designed or selected for amplification of a probe which has hybridised to its target nucleotide sequence. As is described in more detail below, in a certain preferred embodiments the probe may be designed to be ligated if it has hybridised to its target nucleotide sequence, e.g. a ligation reaction designed to circularise the probe. Probe ligation is thus indicative of the presence of the target sequence. A ligated (e.g. circularised) probe may be detected by amplification of the ligated probe, for example by generating an amplification product using the ligated probe as template (e.g. a circularised probe may be a template for a RCA reaction) and the amplification product may be detected, either directly, or by using a detection probe which hybridises to the amplification product.

The AST test of step (f) may, as described further below, be performed in any convenient or desired way. Accordingly microbial growth may be assessed (or determined) in the presence of different antimicrobial agents (e.g. antibiotics) and/or amounts or concentrations of antimicrobial agent (e.g. antibiotic). Growth may be assessed directly or by assessing (determining) markers of growth.

Accordingly, microbial growth may be assessed by determining the amount of microbial cell matter (that is microbial biomass) present in a sample, particularly by assessing or determining this directly. In a preferred embodiment this is achieved by determining the amount of microbial biomass visually, and especially by imaging. In particular 2-D images may be obtained and assessed. Thus in a preferred embodiment the area of microbial biomass may be determined (more particularly the area of microbial biomass in the field of view under investigation, e.g. in an image).

Microbial growth may be assessed by determining the amount of microbial cell matter (that is microbial biomass) present in a sample (here, specifically, in the test microbial cultures set up for the AST test) particularly by assessing or determining this directly. In a preferred embodiment this is achieved by determining the amount of microbial biomass visually, and especially by imaging. In particular, 2-D images aligned perpendicularly to the optical axis (here termed xy-aligned) may be obtained and assessed. A specific area of the specimen is covered in a single xy-aligned image the size of which is dependent on the optical properties of the imaging apparatus. For each position in xy-space, one or more 2D images can be collected at different intervals along the optical or z axis. Thus, a series, or stack of 2D images can be generated, providing 3D information of a sample volume. An alternative method of extracting 3D information from a sample is that employed by Unisensor (see e.g. U.S. Pat. No. 8,780,181), where the optical axis is tilted with respect to the xy-plane, and the sample or detector is moved along either the x or y plane. Here, a series of images with an extension into z space, in addition to xy space, is acquired. Through a subsequent transformation of the image data, stacks of 2D images aligned perpendicularly to the xy plane can be achieved also with this method.

Once extracted, the 3D information inherent in the 2D image stacks can be utilized to estimate/infer/deduce the total cell mass present in the analysed volume. In a preferred embodiment, 2-D images may be generated from 3-D information by e.g. projections of z-stacks into one 2-D image. Analysis may then be performed using the resulting 2-D image. The area of microbial biomass may then be determined as the area of optical density indicating microbial biomass in the field of view under investigation, e.g. in the projected 2D image. Such a method is common practice in the art and may increase sensitivity, and algorithms for this for bright field images may be found in the publicly available software Cellprofiler from MIT, USA. Similar analysis may be performed for fluorescent images, and many alternative algorithms for this exist, e.g. in Cellprofiler, and also in most commercial image analysis systems.

In another embodiment, intensity variation in the z space stretching over each position in xy space is registered, indicating microbial mass in a specific position. Integrated over the entire xy space, this gives a measure of total microbial volume. Algorithms for this procedure also exist in commonly available image analysis software, e.g. in the freeware Cellprofiler.

More generally, microbial growth may be assessed by determining the amount and/or number and/or size of microorganisms and/or microbial colonies or aggregates. As will be discussed in more detail below, in certain preferred embodiments, microbial growth is assessed (determined) by imaging, or alternatively expressed, by visualising the microorganisms. Thus microbial cells, which may include aggregates or clumps (clusters) of cells, or microbial colonies, may be visualised or imaged as a means of determining (or assessing or monitoring) growth. This may include counting of cells or colonies, but is not limited to such methods and includes any means of visually assessing the amount of microbial growth by assessing (or determining) the size, area, shape, morphology and/or number of microbial cells, colonies or aggregates (the term "aggregate" includes any collection of cells in physical proximity e.g. a clump or cluster; this may include non-clonal clumps/clusters of cells which have aggregated or stuck together (e.g. neighbouring cells which have become aggregated) as well as clonal colonies). The parameter used to measure microbial growth may, but need not, vary according to the identity of the microbe (determined in step (e)) and the antimicrobial agents used in step (f). Indeed, depending on the organism and the antimicrobial agents used, the morphology or growth pattern of the cells may be affected, and this may be altered or changed from the "normal" or "typical" morphology or growth pattern, e.g. in the absence of the antimicrobial agent. Whilst some AST growth monitoring methods may depend on detecting such changes, it is not essential according to the present invention to take such changes into account and the amount (e.g. area) of microbial growth or biomass may be determined irrespective of morphology and/or growth pattern. Thus the same growth monitoring method may be used regardless of the microbial cell and/or antimicrobial agents used. Methods for performing the AST test are described further below.

Advantageously, the clinical sample (e.g. a test aliquot) may be used directly in the AST test, after a positive result in step (e). The clinical sample/portion/test aliquot/aliquot fraction etc. would have been subjected to culture during the time that steps (d) and (e) have been performed, and it is not necessary for any further sub-culture to be performed before step (f). Indeed, in advantageous embodiments there is no further sub-culture step. In particular there is no sub-culture step in a further culture medium or culture vessel. More particularly, there is no step of sub-culturing to obtain a pure culture of a microorganism prior to AST. This means that a more rapid AST test may be performed.

Advantageously, a rapid AST test is performed. Accordingly, in a preferred embodiment the AST test of step (f) may give a result in 8, 7, or 6 hours or less, for example in 4 or 5 hours or less.

The monitoring or assessing of microbial growth in the AST test may take place by monitoring growth continuously or at intervals over a time period (e.g. up to 6, 5, 6, 7 or 8 hours), or by comparing growth at the time the AST growth culture is initiated (to) with growth at a later time point (e.g. at up to 4, 5, 6, 7, or 8 hours), or indeed comparing growth at two or more different time points. In preferred embodiments, microbial growth is determined at more than one time point, i.e. at at least two time points.

The method of the invention may be used for the detection and characterisation of any microorganism. Generally speaking clinically relevant microorganisms are concerned. As used herein, the term microorganism encompasses any organism which may fall under the category of "microorganism". Although not necessarily so, microorganisms may be unicellular, or may have a unicellular life stage. The microorganism may be prokaryotic or eukaryotic and generally will include bacteria, archaea, fungi, algae, and protists, including notably protozoa. Of particular interests are bacteria, which may be Gram-positive or Gram-negative or Gram-indeterminate or Gram-non-responsive, and fungi.

Particularly, clinically relevant genera of bacteria include *Staphylococcus* (including Coagulase-negative *Staphylococcus*), *Clostridium, Escherichia, Salmonella, Pseudomonas, Propionibacterium, Bacillus, Lactobacillus, Legionella, Mycobacterium, Micrococcus, Fusobacterium, Moraxella, Proteus, Escherichia, Klebsiella, Acinetobacter, Burkholderia, Entercoccus, Enterobacter, Citrobacter, Haemophilus, Neisseria, Serratia, Streptococcus* (including Alpha-hemolytic and Beta-hemolytic Streptococci), *Bacteroides, Yersinia,* and *Stenotrophomas*, and indeed any other enteric or coliform bacteria. Beta-hemolytic Streptococci would include Group A, Group B, Group C, Group D, Group E, Group F, Group G and Group H Streptococci.

Non-limiting examples of Gram-positive bacteria include *Staphylococcus aureus, Staphylococcus haemolyticus, Staphylococcus epidermidis, Staphylococcus saprophyticus, Staphylococcus lugdunensis, Staphylococcus schleiferei, Staphylococcus caprae, Staphylococcus pneumoniae, Staphylococcus agalactiae Staphylococcus pyogenes, Staphylococcus salivarius, Staphylococcus sanguinis, Staphylococcus anginosus, Streptococcus pneumoniae, Streptococcus pyogenes, Streptococcus mitis, Streptococcus agalactiae, Streptococcus anginosus, Streptococcus equinus, Streptococcus bovis, Clostridium perfringens, Enterococcus faecalis,* and *Enterococcus faecium*. Non-limiting examples of Gram-negative bacteria include *Escherichia coli, Salmonella bongori, Salmonella enterica, Citrobacter koseri, Citrobacter freundii, Klebsiella pneumoniae, Klebsiella oxytoca, Pseudomonas aeruginosa, Haemophilus influenzae, Neisseria meningitidis, Enterobacter cloacae, Enterobacter aerogenes, Serratia marcescens, Stenotrophomonas maltophilia, Morganella morganii, Bacteroides fragilis, Acinetobacter baumannii* and *Proteus mirabilis*.

Clinically relevant fungi may include yeasts, particularly of the genus *Candida*, and fungi in the genera *Aspergillus, Fusarium, Penicilium, Pneumocystis, Cryptococcus, Coccidiodes, Malassezia, Trichosporon, Acremonium, Rhizopus, Mucor* and *Absidia*. Of particular interest are *Candida* and *Aspergillus*. Non-limiting examples of fungi include *Aspergillus fumigatus, Candida albicans, Candida tropicalis, Candida glabrata, Candida dubliensis, Candida parapsilosis,* and *Candida krusei*.

The term "detecting" refers broadly to any means of determining the presence or absence of a microorganism. Thus "detecting" may include determining, assessing or measuring in any way or form whether or not a microorganism is present—it may include qualitative, quantitative or semi-quantitative determinations.

The term "characterising" means broadly any means of determining information about the nature and/or properties of the microorganism, and includes particularly identifying the microorganism. More particularly the microorganism may be identified in terms at least of its genus, and preferably its species. In some cases even identification at the level of strain may be possible. The method of the invention also allows the microorganism to be characterised in terms of determining whether or not it is susceptible, or is expected to be susceptible, to given antimicrobial agents, or whether it demonstrates resistance or is expected to be resistant to any antimicrobial agents e.g. determining its antimicrobial susceptibility profile. This may be done by testing for the presence of molecular resistance markers, namely genetic variants or particular genetic sequences which are associated with, or indicative of resistance to one or antimicrobial agents, or classes of antimicrobial agent. Such molecular tests of course do not determine conclusively that the microorganism is susceptible and this is done by the AST test of step (f) in which the effect of the antimicrobial agent on the growth of the microorganism is tested directly.

The term "lysing" means breaking down of a cell. In particular, the cell is broken down to release cell contents, including particularly nucleic acid, This may be achieved by any means, as vast number of which are known in the art, for example n by viral, enzymatic, mechanical, electrical, chemical, heat, cold or osmotic mechanisms that compromise its integrity leading to the partial or full release of cellular components into surrounding solution.

The clinical sample may be any clinical sample that may be obtained from a test subject, which generally will be a human patient but may be any human or animal, generally mammalian, subject. It may thus be any sample of body tissue, cells or fluid, or any sample derived from the body, e.g. a swab, washing, aspirate or rinsate etc. Suitable clinical samples include, but are not limited to, blood, serum, plasma, blood fractions, joint fluid, urine, semen, saliva, faeces, cerebrospinal fluid, gastric contents, vaginal secretions, mucus, a tissue biopsy sample, tissue homogenates, bone marrow aspirates, bone homogenates, sputum, aspirates, wound exudate, swabs and swab rinsates e.g. a nasopharyngeal swab, other bodily fluids and the like. In a preferred embodiment, the clinical sample is sample is blood or a blood-derived sample, e.g. serum or plasma or a blood fraction.

The microorganism may be any microorganism, in particular any pathogenic microorganism or any microorganism causing an infection in the body, and thus the method may be used in the context of detecting or diagnosing a microbial infection in or on any part of the body of a test subject (i.e. any microbial infection) and the nature of the clinical sample may be determined accordingly, e.g. according to the presentation of symptoms of the infection or suspected infection, or the general clinical condition of the subject. Although any microbial infection is encompassed, the method of the invention has particular utility in the detection or diagnosis of sepsis, or where sepsis is suspected. Thus the clinical sample may be from a subject having, or suspected of having, or at risk of, sepsis. In such a case the sample will generally be blood or a blood-derived sample. Typically the sample will be blood.

In the first step of the method (step (a)) the sample is introduced to a culture vessel comprising culture medium. This is a standard step which may be carried out according to standard procedures well known in the art and widely described in the literature.

A culture vessel can include any vessel or container suitable for the culture of microbial cells, e.g. a plate, well, tube, bottle, flask etc. Conveniently, where the sample is blood or a blood derived sample the culture vessel is a blood culture flask, for example a BacT/ALERT (Biomerieux) blood culture flask, a Bactec blood culture flask (Becton Dickinson) or VersaTrek blood culture flask (Thermo Fisher), or indeed any tube, flask or bottle known for the sampling of blood, particularly for the purpose of culture to detect microorganisms.

Conveniently the culture vessel may be provided with the culture medium already contained therein. However, the culture medium may be separately provided and introduced into the culture vessel, either prior to, simultaneously with, or after the clinical sample has been added.

The culture medium may be any suitable medium and may be selected according to the nature of the clinical sample and/or the suspected microorganism, and/or clinical condition of the subject etc. Many different microbial culture media suitable for such use are known. Typically the culture medium may contain sufficient nutrients to promote rapid growth of microorganisms, as is known in the art. In many cases appropriate media are complex growth media comprising media such as tryptic soy broth, Columbia broth, brain heart infusion broth, Brucella broth, as well as general purpose growth media known in the art, and may include the addition of particular growth factors or supplements. Culture media are available in various forms, including liquid, solid, and suspensions etc. and any of these may be used, but conveniently the medium will be a liquid medium. Where the culture vessel is a ready to use blood culture flask, as described above, these vessels may contain specified media especially modified to allow a wide range of microorganisms to grow. Typically medium supplied in a blood culture flask by a manufacturer will contain an agent or additive to neutralise the presence of any antibiotics present in a clinical sample taken from a test subject. Flasks containing or not containing such neutralising agents may be used, and neutralising agents may be added to the culture vessel if desired.

As noted above, a first test aliquot for the identification tests of step (e) may be removed immediately or substantially immediately after the sample is contacted with the culture medium in the culture vessel, whether from the first or second culture vessel (e.g. after mixing the sample and medium). This may for example be within 10, 15, 20 or 30 minutes of introducing the sample to the culture vessel, or it may be longer, e.g. within 1, 2 or 3 hours, depending on the clinical situation.

Step (b) is an optional step of pre-culturing the clinical sample in the culture vessel (or the portion from the first culture vessel that is introduced into the second culture vessel), that is of allowing any microorganisms present in the sample to grow (i.e. multiply), before the molecular testing takes place. Whether or not this is performed may depend on the nature of the sample, and the suspected infection, clinical status of the subject etc. For example, in the case of a urine sample, a high number of microbial cells are expected to be present in the sample and hence a pre-culture step may not be required, However, in the case of a blood sample for example, the number of cells is generally expected to be less and a pre-culture step may be advantageous to increase the number of microbial cells available for molecular testing, or to facilitate recovery of microbial DNA etc. This may also depend on the nature of the molecular tests (i.e. probes) used for the microbial identification and resistance marker detection and the sensitivity and/or specificity of the nucleic acid tests.

Pre-culturing generally involves incubating the culture vessel under conditions conducive to, or suitable for, microbial growth e.g. at a particular temperature (for example, at a temperature from 20 to 40° C., or 25 to 40° C. e.g. 25 to 37° C., or 30 to 35° C. Depending on the nature of the vessel, medium, suspected microorganism, clinical condition etc., the vessel may be agitated or rotated, shaken etc.

Pre-culturing can take place for any suitable or desired time period, but in order to speed up the method it will preferably be for a short time period of less than 8 or less than 6 hours. For example pre-culture may take place for up to 1, 2, 3, 4, 5 or 6 hours prior to the commencement of testing, or more particularly prior to removal of the test aliquot in step (c). Alternatively preculturing can take place for less than 1 hour. Preculturing can also take place for more than 6 hours, for example for 7, 8 or 9 hours, or more than 9 hours, for example up to 10, or 12 hours, or even longer, but in the interests of providing a rapid method it is generally kept to a minimum, and short pre-culture periods of up to 6, or more particularly up to 4 or 3 hours are preferred. As noted above, preculture may take place for a period shorter than is required to see a positive culture result or it may take place until a positive culture result is obtained.

Removal of the test aliquot in step (c) may take place by any convenient means, depending on the nature of the culture vessel and how it is incubated. For example in the case of a blood culture flask an aliquot may simply be withdrawn using a needle and syringe. According to normal clinical and microbiological practice steps may be taken to avoid or limit contamination, e.g. this may be done under aseptic conditions. For example, the septum of a culture vessel, such as a blood culture flask, may be cleaned or decontaminated, preferably prior to withdrawing an aliquot, and/or after withdrawing an aliquot.

In one convenient embodiment, the means for removal of the test aliquot (e.g. the needle, and optionally the syringe, may be provided in single-use form, i.e. as a consumable. In other words it may be disposable and not re-used.

Step (c) of removing a test aliquot while continuing to culture may be performed more than once. Indeed, for performing the molecular tests of step (e) and the AST test of step (f) two separate aliquots will usually be taken and in each case culture will be continued. As mentioned above, however, a portion of the aliquot taken for performing the molecular tests may be retained and cultured. This portion may be used for repeat molecular tests (e.g. at a second time point) and/or may be used in the AST test. However, separate aliquots for repeat molecular tests may also be taken, for example at spaced intervals of time. Thus a molecular test (step e) may be performed more than once. In one such embodiment, an aliquot may be removed straight after step (a) for an initial molecular test to be performed prior to a pre-culturing step (b). If the initial molecular test is negative or not fully conclusive for example, a second aliquot may be removed after a period of preculture to carry out a second molecular test. Thus in one embodiment, a method of the invention may comprise the following steps:

i) introducing a clinical sample to a culture vessel containing culture medium;
ii) removing a test aliquot from said culture vessel,
iii) separating DNA from said test aliquot and performing nucleic acid tests as described in step (e) above;
iv) whilst step (iii) is ongoing culturing said clinical sample in said culture vessel;
v) removing a further test aliquot from said culture vessel, and continuing to culture said clinical sample in said culture vessel;
vi) separating DNA from said further test aliquot and performing nucleic acid tests as described in step (e) above;
If this second (or any further) molecular test is negative the method may proceed to step (g). Thus, culturing of the culture vessel may be continued to allow further tests to be performed.

To enable the molecular nucleic acid tests of step (e) to be performed, DNA is separated from the removed aliquot or aliquot fraction (in step (d)). It will be understood of course that microbial DNA is required for the molecular tests and depending on the nature of the clinical sample there may be a significant number of cells from the test subject present, which may complicate or interfere in the separation or subsequent testing. More particularly the non-microbial DNA, e.g. human DNA, present in the cells of the test subject in the clinical sample may make the detection and testing of microbial DNA difficult, particularly in the case of samples such as blood where there are very many more blood cells (particularly white blood cells) than microbial cells. Accordingly it may be desirable to selectively separate, or enrich for, microbial DNA from the test aliquot. Indeed the method may optionally comprise a step of separating or enriching microorganisms or microbial cells in or from the test aliquot, e.g. prior to or concurrently with the step of separating DNA, or separating microbial DNA.

Suitable methods for enriching the microorganisms in the sample can include lysing any non-microbial cells present in the aliquot, or selectively removing microbial cells from the aliquot (i.e. positive or negative selection of microbial cells from the aliquot). Methods for doing this are known in the art. Methods for selectively lysing non-microbial cells for selectively enriching microorganisms in a sample, which are not dependent on knowing the identity of the microorganisms, are described for example in US 2013/0171615, US 2012/0231446, US 2010/0184210, U.S. Pat. Nos. 7,893,251 and 8,481,265, and methods for selectively removing eukaryotic cells from a sample are described in US 2005/0202487.

Methods for separating DNA are known in the art, and any of the various different methods known and described may be used. Generally speaking these involve lysing cells, which may be done by various means and ways, and recovering the released DNA, and again various means and procedures for this are known and available and any of these can be used. The lysis step may depend on the nature of the suspected microorganisms, although many procedures may lyse microorganisms in general.

As mentioned above, depending on the nature of the sample, preferably this step involves separating microbial DNA, more particularly selectively separating, or enriching for, microbial DNA. This may generally be done by selectively lysing test subject cells in the sample, whilst leaving the microbial cells intact. Many procedures, and indeed kits, are known and available which can achieve this, for example from Molzym (Germany). For example, human cells, e.g. human blood cells, may readily be lysed, without lysing microbial cells present in the aliquot. The same applies to other human or mammalian cells which may be present, depending on the sample. Separation, and in particular selective separation, of microbial DNA is preferred in the case of a blood or blood-derived sample.

Thus any cells in the clinical sample which derive from the subject under test and which are present in the test aliquot may be lysed using lysis conditions which do not lyse microbial cells. For example an appropriate lysis reagent, e.g. a lysis buffer, may be added to the test aliquot. The DNA, or nucleic acid more generally, released in this first lysis step may be removed, for example by degradation (e.g. with a DNA-degrading enzyme e.g. DNase), and/or by any method which can separate or remove DNA or nucleic acid from the sample and/or separate any non-lysed microbial cells, e.g. a separation method such as filtration, column separation, precipitation, centrifugation etc., although in one embodiment it is preferred feature of the method that it does not include centrifugation. Thus in one embodiment the step of DNA separation does not include centrifugation, and indeed in a further preferred embodiment the method as a whole does not include centrifugation. Any enzymes, particularly any DNA-degrading enzymes, used in these steps may be inactivated or removed, e.g. by heating or by adding further protein-degrading enzymes.

Next, microbial cells remaining in, or from, the treated aliquot (e.g. the lysate from the first lysis step) are then lysed by introducing lysis conditions, e.g. adding an appropriate lysis reagent (e.g. lysis buffer) for lysis of microbial cells. Many such buffers are known in the art and/or commercially available e.g. from Molzym (Germany). Microbial DNA released in the second microbial lysis step may then be recovered, e.g. separated from the reaction mixture (lysate). As above, many techniques for this are available and any of these may be used. In a preferred embodiment this step does not include centrifugation.

The recovered DNA, or recovered microbial DNA, is then subjected to the molecular tests of step (e). It may be desirable to denature double-stranded DNA, particularly microbial DNA separated or enriched from the test aliquot, prior to performing the molecular nucleic acid tests of step (e). Further it may be advantageous or desirable (but is not necessary) to fragment the DNA prior to performing the molecular tests of step (e). Such steps may be achieved by routine methods known in the art, for example fragmentation may achieved mechanically, by heat or by enzymatic degradation methods, e.g. using restriction or other endonucleases.

Essentially the molecular tests use nucleic acid probes or primers which are designed to hybridise to specific microbial nucleic acid sequences, or to be capable of selectively amplifying a specific microbial sequence, and which, based on whether or not they hybridise, or are extended (e.g. successfully prime an amplification reaction) can be used to detect whether or not a particular microorganism is present and whether or not it contains a genetic antimicrobial resistance marker. Such nucleic acid tests, and hybridisation probes or primers for use in them, are known in the art and described in the literature.

A hybridisation probe will comprise a nucleotide sequence which is capable of hybridising to a desired or selected target sequence, preferably specifically hybridising. Thus it may comprise a sequence which is complementary to a target sequence. Absolute or 100% complementarity is not required as long as the probe is capable of hybridising specifically to the target sequence in the presence of non-target nucleotide sequences. By detecting hybridisation it can be detected whether or not the target sequence is present, and many hybridisation assay formats using different modalities for detecting hybridisation of a nucleic acid probe are known and may be used. Generally speaking, the detection of step (e) may take place by detecting the hybridisation probe.

As discussed above, detection of the hybridisation probe may comprise or involve amplifying the hybridisation probe. Accordingly, in addition to hybridisation probes, one or more amplification primers for the hybridisation probes may be provided.

In the case of the invention the target sequence is firstly (in step (e)(i)) a nucleotide sequence identificatory of a microorganism, that is, a nucleotide sequence which is characteristic of a particular microorganism, e.g. of a genus, species or strain and which may be used as the basis for identifying that microorganism. Thus the identificatory nucleotide sequence may accordingly be viewed as a motif or signature, or sequence characteristic of a given particular microorganism. Typically it may be a sequence which is unique to that microorganism (e.g. at genus, species or strain level). A number of such identificatory sequences have been identified and reported and any of these could be used. For instance the target sequence may be a nucleic acid sequence from the 16s rRNA gene. Alternatively it would be a routine matter to identify such motif/signature/identificatory sequences, e.g. using bioinformatic tools to analyse microbial genomic sequences, and to design appropriate hybridisation probes based on these, comprising sequences capable of hybridising to the identified sequences.

Alternatively, rather than using hybridisation probes, one or more primers may be used and a primer-based method, for example a polymerase primer extension-based method, may be used to detect and identify the microorganism. Typically this will be an amplification method, most commonly PCR, but other amplification methods or primer extension methods may be used, including e.g. LCR, NASBA, MDA etc. A primer or set of primers may hybridise to the identificatory nucleotide sequence, or it (they) may hybridise in such a manner (e.g. flanking it) that an identificatory sequence may be amplified. The term "amplified" is used broadly in this context (see also above) to mean any method of providing a copy (including a complementary copy) of the identificatory or marker sequence and includes simple primer extension reactions, and linear as well as exponential amplification. For PCR, a primer pair will be used for each microbial identificatory sequence.

Put more simply, the hybridisation probes or primers for use in the invention may be specific for (i) a nucleotide sequence which is identificatory of a microorganism or (ii) a nucleotide sequence representing a genetic antimicrobial resistance marker.

Thus, alternatively defined, in the method of the invention as set above, step (e) may be expressed as follows:

e) performing nucleic acid tests on said DNA to identify the microorganism and to detect the presence or absence of one or more genetic antimicrobial resistance markers in said microorganism, wherein said nucleic acid tests are performed using:

i) one or more nucleic acid probes and/or primers for microbial identification, each said probe and/or primer being specific for a nucleotide sequence which is identificatory of a given microorganism; and ii) one or more nucleic acid probes and/or primers for antimicrobial resistance marker detection, each said probe and/or primer being specific for a nucleotide sequence representing a genetic antimicrobial resistance marker;

and it is detected whether or not said probes or primers have hybridised to said DNA and/or said primers have been extended (e.g. an amplification reaction has taken place).

As noted above, the detection step may comprise or involve amplifying a probe after it has hybridised to its target nucleotide sequence. As described in more detail below, amplification may be designed to be dependent on hybridisation. Thus, only a probe which has hybridised may be amplified.

In this way a set or panel of hybridisation probes or primers can be assembled and/or constructed which are capable of hybridising to, or amplifying, the nucleic acids of selected microorganisms and thereby detecting whether or not that microorganism is present in the test aliquot (and thereby sample). By detecting which microorganism is present (i.e. which identification probe hybridises or which primer/primer set is extended or primes an amplification reaction), it may be identified which microorganism is present in the sample. By way of example the hybridisation probes or primers for microbial identification may comprise probes or primers each capable of specifically identifying one of a selected set of microorganisms, e.g. the major or most common known sepsis pathogens. For example the lists of specific bacterial and fungal species provided above represent approximately 95% of the most common sepsis pathogens and may constitute a representative microorganism panel according to the invention.

Accordingly, in step (e)(i) a multiplicity of identification probes and/or primers (or primer sets) will advantageously be used. A multiplicity is broadly defined herein as two or more, or more particularly, 3, 4, 5, 6, 7, 8, 9, 10, 15, 20, 30, 40, 50, 60, 70, 80, 100, 200, 300, 400 or 500 or more. As well as multiple different microorganisms for identification, different probes or primers/primer sets may be used for a given microorganism to be detected, e.g. 2, 3, 4 or 5 probes or primers, or more per target microorganism. Since a panel of microorganisms may include at least 10, 15, 20, 25, 30, 40, 50 or more (e.g. up to 60, 70, 80, 90 or 100 microorganisms, typically a panel or set of at least 30 or more, e.g. 50, 70, 80, 100, 200, 300, 400 or 500 or more identification probes or primers (or primer sets) will be used. According to procedures known in the art, probe or primer-based nucleic acid test may use thousands, or many tens or thousands, of probes or primers in multiplex and such procedures are encompassed by the present invention.

Secondly, in step (e)(ii) of the method, the target sequence for the hybridisation probes or primers is a nucleotide sequence which is an antimicrobial resistance marker. A number of such markers have been identified and reported in the art and hybridisation probes/primers to detect them have been devised. Any of these could be used or alternatively further probes or primers may be designed based on such identified marker sequences. Further, additional marker sequences may be identified by routine screening methods. An antimicrobial resistance marker may be a nucleotide sequence which codes for a component of a resistance mechanism e.g. an enzyme or a modified protein, or it may simply be a nucleotide sequence or sequence variant which has been identified to associate with resistance to an antimicrobial agent.

By way of example, β-lactamases represent an important mechanism of resistance against antibiotics for bacteria and are responsible for resistance to certain antibiotic classes. The emergence of bacteria capable of forming extended spectrum β-lactamases (ESBL-forming bacteria). ESBL represents a recent example of a rapidly developing resistance problem. Probes have been reported capable of identifying highly diverse β-lactamases (Barisic et al, 2013, Diagnostic Microbiology & Infectious Disease, 77(2), 118-125). Other known genetic resistance markers include mecA, mecC, vanA, vanB, CTX-M, KPC, VIM, NDM, and OXA-48. Ciprofloxacin resistance mutations have been identified e.g. in antibiotic-resistant *F. tularensis, B. anthracis*, and *Y. pestis*, and are available.

Hybridisation probes may take various forms, and at their simplest comprise a nucleotide sequence capable of hybridising to the target sequence and a further sequence or moiety by which they may be detected, directly or indirectly. Thus such a probe may be provided with a directly or indirectly detectable label, e.g. a spectrophotometrically (e.g. fluorescently) detectable label, or a reporter molecule or moiety which may take part in a signal-giving or signal generating reaction e.g. an enzyme, or enzyme substrate or co-factor, or which may be an affinity tag by which the probe may be selectively labelled or selectively isolated or separated after the hybridisation reaction. Different forms of labelling and labelled nucleic acid probes are widely known and reported e.g. molecular beacons and other FRET based probes. However, rather than directly detecting the presence of a hybridised probe by means of a label or reporter moiety provided in or on the probe, the probe may be detected indirectly, for example by detecting an amplification product to the probe. Different hybridisation probe formats are known and any of these may be used, for example, molecular inversion probes, scorpion probes and padlock probes.

Molecular inversion probes and padlock probes for example are designed to be circularised by ligation following hybridisation to their target sequence, and the resulting circularised probe may be detected by amplification, e.g. by RCA.

Padlock probes represent a preferred type of hybridisation probe according to the present invention. Padlock probes were initially described in 1994 (Nilsson et al, 1994, Science, 265, 2085-2088) and have since been developed and widely used in the detection of various nucleotide sequences, and indeed more widely as reporters in the assay of wide range of molecules (see e.g. EP0745140, EP0964704, EP0951565 and Hardenbol et al. 2003. Nat. Biotechnol. 21, 673-678) Padlock probes comprise sequences at their 5' and 3' ends that can hybridise to a target nucleotide sequence. In one embodiment, the 5' and 3' ends of the padlock probes can hybridise to said nucleotide sequence so that they are directly adjacent to each other. In another embodiment the 5' and 3' ends of the padlock probes can hybridise to said nucleotide sequence so that they are not directly adjacent to each other and the intervening gap may be filled in, either by polymerase extension of the hybridised 3' end, or by a gap-filling oligonucleotide. The ends are then ligated together to form a nucleic acid circle which can subsequently be detected, conveniently by rolling circle amplification (RCA)-based methods. The dual recognition (two target hybridising regions) as well as the requirement for ligation means that padlock probes are highly specific and well suited to detecting unique sequences in a complex genomic background. The uni-molecular circularisation approach and the RCA-based detection of the circularised probes both lend themselves well to multiplexed detection, and a large number of probes may be used in combination and amplified together without problems of interference.

However, although RCA is a preferred method for detecting a circularised padlock probe, the invention is not limited to this and other amplification methods, including e.g. PCR, or other detection methods e.g. based on selectively detecting circular as opposed to linear nucleic acids, may be used.

Strand-displacing polymerase enzymes suitable for RCA are known, e.g. Φ-29 polymerase.

Amplification of a circularised padlock probe by RCA leads to the formation of a concatemeric RCA product comprising several hundreds of repeats of the complement of the padlock probe sequence. In one embodiment of the present invention an RCA product may be detected by hybridisation of fluorescently-labelled detection oligonucleotides.

Since the RCA reaction is linear, and thus has slow amplification power, a number of methods have been developed which may enhance amplification and increase the signal from an RCA reaction, including for example hyperbranched RCA methods as described by Lizardi (U.S. Pat. Nos. 6,183,960 and 6,143,495). Any of these may be used. The RCA product can also be amplified further by PCR, or indeed any other method of nucleic acid amplification or any signal amplification method may be used.

A particularly useful method for enhancing RCA amplification is Circle-to-Circle Amplification (C2CA). This is described in Dahl et al, 2004, PNAS USA, 101, 4548-4553 and WO 03/012199. C2CA involves cleaving the concatemeric rolling circle amplification product (RCP) from a first RCA reaction into monomers (e.g. each corresponding to a tandem repeat of the concatemer, i.e. a complementary copy of the circularised padlock probe) and then recircularsing the monomers, each into a further circle which may be used as the template in a further RCA reaction (i.e. a further round of RCA). This may be repeated one or more times. The repeat RCAs lead to amplification of the signal.

Cleavage of the RCP may be achieved by hybridising an oligonucleotide to a sequence (restriction site sequence) present in each repeat (monomer) of the RCA product to create a double-stranded restriction cleavage or recognition site and cleaving with a restriction enzyme to cleave the product into monomers. The same oligonucleotide, e.g. added in excess, may be used as the ligation template for circularisation of the monomers released by the cleavage. A denaturation step may be included after cleavage to release single stranded monomers, which are available for hybridisation to excess uncleaved or added oligonucleotide.

A modification of the C2CA reaction is described in our co-pending application UK patent application No. 1321123.0 filed on 29 Nov. 2013, herein incorporated by reference. In this modified C2CA procedure the efficiency of the second or any subsequent round of RCA is improved by reducing the size of the circularised monomers, such that the circular template for the second round of RCA is reduced in size as compared to the first RCA template (here the circularised padlock probe), and thereby the speed of the second (and subsequent) RCA reactions may be increased. Various means of cleaving the RCP such that the released monomers are reduced in size or for otherwise effecting a size reduction step on the monomers are described in the co-pending application.

Other ways of amplifying the signal from an RCA reaction by performing a second RCA reaction have also been reported and any of these may be used. One such method is the so-called superRCA (sRCA) method of Olink AB described in WO 2014/076209. In this procedure a second RCA reaction is performed, which is dependent upon a first RCA reaction, but which does not amplify the first RCA product. The second RCA product remains physically attached to the first RCA product, in order that the signal from the second RCA product is localised to the first RCA product. By utilising an RCA primer which is hybridised (directly or indirectly) to the first RCA product to amplify a second RCA template circle, a second RCA product may be generated by extension of the RCA primer, which, by virtue of hybridisation of the primer, is hybridised, and hence attached to the first RCA product. Since the first RCA product is a concatemer comprising tandem repeat complementary copies of the template circle for the first RCA reaction, the RCA primer for the second RCA will bind to repeated copies of its cognate primer-binding sequence, repeated throughout the first RCA product. In other words, the first RCA product will comprise repeated binding sites for the RCA primer for the second RCA, one in each of the tandem repeats ("monomers" of the concatemer). Each such primer can prime a second RCA reaction, leading to increased, more than linear, amplification.

The RCP of an RCA or C2CA reaction may be detected directly, as indicated above, e.g. by means of labelled detection oligonucleotides which can hybridise to sequences in the tandem repeats in the RCP or by incorporating labelled nucleotides into the RCP, or monomers released from an RCP may be detected.

An RCP, being a very long nucleic acid concatemer (typically comprising 500-1000 copies of the template circle sequence), collapses into a random-coiled amorphous "blob" or ball of DNA, which can readily be detected, and indeed visualised. Thus such blobs may be imaged or detected microscopically or by any other convenient means, to detect (indirectly) hybridisation of the padlock probes to their targets (and their subsequent ligation and detection by RCA/C2CA). Other means of detecting the RCP also exist, for example by flow cytometry, or by capturing the RCP on a solid support and detecting it by means of labelled detection oligonucleotides or other labelling means, e.g. incorporated labelled oligonucleotides or nucleic acid stains or dyes etc.

Detection of an RCP blob does provides a convenient means of amplified single molecule detection (ASMD), The use of such a method based on C2CA and counting of RCP blobs to detect bacteria and spores is described by Goransson et al., 2012 PLOS one, 7(2), e31068 and such a method may be used according to the present invention. The concentration, or enrichment, of the label in the RCP blob means that there is a high concentration of label in the blob as compared to the surrounding solution. This eliminates the need for washes and enables homogenous methods to be used—reaction products can readily be detected in a flow cell, for example as described by Jarvius et al., 2006, Nature Methods, 3, 725-727.

Alternatively, rather than detecting the RCP concatemer as such, the RCP can be cleaved into monomers and the monomers may be detected. Again this may be by means of label incorporated directly into the monomers, or by hybridising detection oligonucleotides to the monomers, e.g. as described above, or according to principles well known in the art. For example monomers may be bound onto a microarray and the array-bound (hybridised) monomers may be detected by hybridisation of labelled detection oligonucleotides. Thus an array may be provided which carries (e.g. by depositing on) oligonucleotides that are capable of binding to (hybridise) to the RCP monomers. The array oligonucleotides can be designed to be complementary to the RCP monomers and may be covalently coupled to the array substrate via amine, thiol or epoxide groups or by any known coupling chemistry, or they may be synthesised in situ on the array using known techniques e.g. photolithography. Such an array can then be scanned or imaged and analysed, again according to methods well known in the art. Thus, it can be detected whether or not a particular padlock probe was hybridised to its target and therefore ligated and amplified, by detecting whether or not a particular RCP monomer has been hybridised to the array.

Thus, in certain embodiments of the present invention, solid phase-based methods may be used. A solid support may be employed in carrying out various stages or steps of the method. For example, as well as or alternatively to the possible array detection of RCP monomers discussed above, a solid phase may be used in earlier steps of the method. In one such embodiment the target DNA from or in the DNA separated from the test aliquot for use in molecular testing may be immobilised on a solid support. Thus DNA fragments or DNA molecules which may comprise the nucleotide sequences which are the targets for the molecular tests to be carried out in step (e), may be selectively captured from the separated DNA of step (d) using capture probes, e.g. prior to or at the same time as the molecular testing. Capture probes may be used which hybridise to the target DNA (at sites distinct from the hybridisation sites for the nucleic acid identification and resistance detection probes or primers). The capture probes may be added to the separated or enriched DNA, e.g. prior to or at the same time as the identification and resistance detection probes or primers. The capture probes may be immobilised or provided with means for immobilisation such that they may be immobilised after binding to the target DNA. Such means for immobilisation may include for example an affinity molecule capable of binding to its cognate binding partner, provided on a solid support. By way of representative example the capture probe may be biotinylated, for binding to streptavidin or avidin (or a variant thereof) which is coupled to the solid support. Any convenient solid support may be used, as known in the art. For example a solid support can include a microarray, blotting membrane, gel, microscope slide, well, tube or other container or vessel, or a bead or particle, e.g. a glass, polymer, plastic or magnetic bead or particle. A target DNA molecule may alternatively be immobilised on a solid support directly. Thus in a preferred embodiment of the present invention a target DNA molecule may be immobilised on a solid support conjugated to streptavidin via a biotinylated capture oligonucleotide. In an alternative embodiment of the present invention, a target DNA molecule may be biotinylated and immobilised on a solid support conjugated to streptavidin.

While the molecular tests of step (e) are being performed the culture vessel containing the clinical sample is kept in culture (if a pre-culture step was performed) or it is subjected to a culture step (step (c)). As indicated above, culturing simply involves incubating the culture vessel under conditions suitable for, or conducive to, microbial growth. Thus this step may be performed as indicated for pre-culture above. This step means that if positive microbial identification is not obtained from the molecular tests of step (e), the sample is available for traditional culture based identification protocols based on conventional phenotypic and/or biochemical tests, or indeed for further ID testing by any other means—these tests are not delayed because the culture is on-going, and a further clinical sample does not need to be taken, or further culture started. Indeed at this time, if no microorganism is identified in step (e), then the culture may be continued as is, or the culture vessel may be transferred to another culture system (e.g. an automated culture system or cabinet designed for microbial identification and optionally also antimicrobial susceptibility testing. After an appropriate period of culture such further ID tests and also susceptibility tests may be performed, the latter for example by conventional AST testing means, e.g. by turbidimetrically-assessed broth dilution cultures or disc-diffusion tests to determine MICs.

If a microorganism is identified in the test aliquot, an antimicrobial susceptibility test is performed on the cultured clinical sample that has been kept in culture in step (c). Conveniently, this may involve withdrawing or removing a further (e.g. second or subsequent, depending on how many aliquots have been removed for molecular testing) aliquot from the culture vessel, and performing AST testing on this.

The method may also comprise a further step at this stage of enriching the aliquot or cultured clinical sample for microorganisms. Procedures suitable for this are discussed above, and may include removing or separating non-microbial cells (i.e. test subject cells) from the aliquot/cultured sample. In one embodiment, microbial cells can be separated e.g. by filtration.

Recognised and prescribed conditions for AST testing exist, and may be followed in order that readily comparable results may be obtained which are comparable to, or may be compared with, tests performed in other laboratories. This may involve for example the use of a prescribed medium and culture conditions. Thus, the further removed aliquot (or aliquot fraction/remainder etc.) for AST testing, or separated or enriched microorganisms therefrom, may be transferred into a suitable medium for microbial culture, for example Mueller-Hinton medium (MH-media), prior to the commencement of the antimicrobial susceptibility test. Microorganisms may be grown in the presence of a variety of antimicrobial agents to determine their susceptibility to a given antimicrobial agent. According to the present invention the antimicrobial agents are selected based on the identity of the microorganism, and on the nature of any genetic antimicrobial resistance markers identified within the microorganism. The antimicrobial agents, and the amounts to be used, may also be selected according to current clinical practice, e.g. according to which antimicrobial agents are currently used in practice to treat the identified microorganism, in order that the susceptibility of the microorganism to the currently accepted or recognised antimicrobial treatment of choice can be assessed. Thus antimicrobial agents can be selected based on those known to be effective against the identified microorganism, or those currently used in practice to treat the microorganism, and excluding any agents to which resistance might be expected based on the presence of resistance markers, or such agents might be included and the amounts used might be selected to allow the determination of an amount or concentration of the antimicrobial agent that may be effective, despite the presence of the resistance marker. Antimicrobial agents are added to growth medium to a range of final concentrations or amounts. In a preferred embodiment of the present invention a serial dilution of the antimicrobial agent may be performed.

The step of growing, or culturing, the sample/microorganisms therefrom in the AST test may take place by any known or convenient means. Solid or liquid phase cultures may be used.

Thus for example, in one preferred embodiment, the sample/microorganisms may be cultured on or in a plate or other solid medium containing the antimicrobial agent and microbial growth may be determined by visualising (e.g. imaging) the microorganisms (i.e. imaging the plate etc.) Thus, the culture is visualised or imaged directly as a means of monitoring or assessing growth. Accordingly in one preferred embodiment the cultures are analysed directly to monitor/assess growth. For example, the cultures may be grown in the wells of a plate and the wells may be imaged.

Alternatively, samples (or aliquots) may be removed (or taken) from the cultures, at intervals, or at different time points and the removed samples (aliquots) may be analysed for microbial growth. This may be done by any means, including for example by means of molecular tests, e.g. nucleic acid based tests, Thus detection probes and/or primers may be used which bind to the microbial cells or to components released or separated from microbial cells. This may include for example nucleic acid probes or primers as described above for the identification test of step (e). In other embodiments, microbial cells may be detected directly, e.g. by staining, as described in more detail below.

Each antimicrobial agent is preferably used at least one concentration, in addition to a positive control in which the microorganism is allowed to grow in the absence of any antimicrobial agent. For example, 2, 3, 4, 5, 6, 7, or 8 or more concentrations of an antimicrobial agent are used. The concentrations used in a dilution series may differ two-fold between respective concentrations.

The term antimicrobial includes any agent that kills microorganisms or inhibits their growth. Antimicrobial agents of the present invention may particularly include antibiotics and antifungals. Antimicrobial agents may be microbicidal or microbiostatic. Various different classes of antibiotic are known, including antibiotics active against fungi, or particularly groups of fungi and any or all of these may be used. Antibiotics may include beta lactam antibiotics, cephalosporins, polymyxins, rifamycins, lipiarmycins, quinolones, sulphonamides, macrolides, lincosamides, tetracyclines, aminoglycosides, cyclic lipopeptides, glycylcyclines, oxazolidinones, lipiarmycins or carbapenams. Preferred antifungals of the present invention may include polyenes, imidazoles, triazoles and thiazoles, allylamines or echinocandins.

Accordingly, antimicrobial susceptibility may be determined by culturing the removed aliquot (or aliquot fraction etc.) or cultured clinical sample from step (c), or microorganisms separated or enriched therefrom, and analysing the AST cultures over a range of time points. As for the culture step above, culture for AST may take place at any temperature that promotes microbial growth, e.g. between about 20° C. and 40° C., or 20 to 37° C., preferably between about 25° C. and 37° C., more preferably between about 30° C. and 37° C. or 30 to 35° C. In one embodiment the AST cultures may be cultured at about 35° C. The AST cultures may be analysed at multiple time points to monitor microbial growth. For example, cultures may be analysed at time points 0, 1, 2, 3, 4, 5, 6, 7, 8, 9, 10, 11, 12, 13, 14, 15, 16, 17, 18, 19, 20, 21, 22, 23 or 24 hours after the initiation of culture. A culture may be analysed immediately after the initiation of culture, where t=0. Cultures may also be analysed at time periods beyond 24 hours after the initiation of culture. Typically cultures might be analysed at 0, 1, 2, 3, 4, 6 and 24 hours after the initiation of culture. However, results obtained and reported in the Examples below show that short incubation times can be sufficient for detecting differential microbial growth e.g. 4 hours. Accordingly, shorter total incubation time of up to 8, 7, 6, 5, 4, 3 or 2 hours may also be used, e.g. analysing every hour or every 2 hours or 90 minutes. As noted above, cultures are generally analysed at two or more time points, e.g. at two or more time points up to 4, 5 or 6 hours of culture.

The present invention requires microbial growth to be monitored during the antimicrobial susceptibility test. Many methods for monitoring microbial growth are known and are used in AST tests, for example including turbimetric measurement, colorimetric determination, light detection, light scattering, pH measurement, spectroscopic measurements and fluorimetric detection. Any of these may be used. However, according to a preferred embodiment of the present invention growth may be detected and assessed by determining or assessing the number and/or amount and/or size and/or area of microbial cells in the sample by imaging methods, As noted above, the microbial cells can include cells in colonies and/or aggregates. This may be achieved by assessing or determining the number or amount of microorganisms present in the sample before and/or after growth in presence of antimicrobial agents by any of the methods known to measure or detect microorganisms. Such a determination may involve determining the number and/or size of microbial cells, aggregates and/or colonies. Again, techniques for this are known and available. Thus, growth may be measured by monitoring the number and/or amount and/or size of microorganisms and/or microbial cells and/or colonies and/or aggregates in a sample over time. This may be measured directly or indirectly. The number or amount of microorganisms in a sample may be measured directly by haemocytometry, flow cytometry, or automated microscopy. Microorganisms may be fixed and/or permeabilised prior to detection. Alternatively, microorganisms may be detected under in vivo conditions. Methods for AST testing by bacterial cell count monitoring using flow cytometry are described in Broeren et al., 2013, Clin. Microbiol. Infect. 19. 286-291. Methods for performing AST tests in which bacteria are grown and enumerated by automated microscopy in multi-channel fluidic cassettes are described by Price et al. 2014, J. Microbiol. Met. 98, 50-58 and by Metzger et al., 2014. J. Microbiol. Met. 79, 160-165, and by Accelerate Diagnostics (see for example WO 2014/040088 A1, US 2014/0278136 A1 and U.S. Pat. No. 8,460,887 B2). In these methods, bacteria are immobilised and grown on a surface, and individual bacteria and/or colonies are assessed for viability and/or growth (including measuring colony growth) by imaging the surface at two or more time points. Such methods may be used according to the present invention. Other methods known are as described by Fredborg et al, J Clin Microbiol. 2013 July; 51(7):2047-53, and by Unisensor (U.S. Pat. No. 8,780,181) where bacteria are imaged in solution using bright-field microscopy by taking a series of stacked images (object planes) of the solution, and counting the bacteria present in the sample.

Whilst any of the methods based on using imaging to monitor microbial growth may be used, the methods of the invention preferably do not rely on counting individual cells or on monitoring the growth of individual cells or colonies (e.g. on monitoring an increase in size of an individual cell or colony e.g. according to the methods of Accelerate Diagnostics Inc.) Thus, the present invention is not limited to (and in preferred embodiments does not involve) using a fixed position for imaging an AST culture or AST culture sample. Rather, it is preferred according to the present invention to monitor the bulk growth of cells in the AST culture or culture sample, e.g. by imaging bulk cells in the field of view. The amount (e.g. area) of microbial cell matter (biomass) in the field of view may be determined by imaging. The cells/microbial biomass may be detected directly (e.g. by the microscope or camera etc.) e.g. using bright field microscopy or the microbial cells may be stained for detection, e.g. by adding stain to the AST culture or culture sample after the predetermined or required time period of growth.

In a further particular embodiment, the AST cultures or culture samples may be imaged or visualised directly without immobilising the microbial cells, e.g. without applying a force, such as electrophoresis, to localise the cells to a detection location or surface for imaging.

In such imaging methods, algorithms may be applied to determine a value for the amount of microbial growth from the images according to methods and principles well known in the art. Thus, statistical methods may be applied to the images of microbial cells, based on the number, size, and/or area of microbial cell matter/biomass in the images (e.g. the amount of all the microbial cell matter in the image/field of view, for example total cell matter imaged). Algorithms may be written to take account of different growth patterns and/or morphologies, based on the identity of the microorganism and the antimicrobial agent present in the culture.

Such counting or imaging methods allow a digital phenotypic analysis of the microorganism in the AST test. Data has been obtained which shows that such digital phenotypic determinations deliver a MIC value similar to that of reference techniques (e.g. microbroth dilution).

A particular advantage of using such methods is that antimicrobial susceptibility testing may be performed on samples comprising a wide range of concentrations or amounts of microorganisms, and it is not necessary to use a standardised microbial titer prior to performing the antimicrobial susceptibility testing. A useful feature of the present invention is the ability to use different concentrations of microorganisms. A sample comprising at least $10^3$ CFU/ml may be used in the methods of the samples, for example samples comprising at least $10^4$, $10^5$, $10^6$, $10^7$ $10^8$ or $10^9$ CFU/ml may be used. Alternatively a sample comprising less than $10^3$ CFU/ml may be used, for example at least $10^2$ CFU/ml. A sample comprising less than $10^2$ CFU/ml may also be used in the methods of the present invention In one embodiment of the present invention, microorganisms may be detected by adding a marker that stains microorganisms (i.e a stain or dye) prior to determining the number or amount of microorganisms in a sample or by methods which utilize an intrinsic property of the microorganism such as e.g. phase contrast or any other method known in the art for quantifying the number of bacteria in the sample. Suitable stains might include coloured or fluorescent dyes, for example Gram staining or other staining for peptidoglycan or DNA staining, as a means of visualising the microorganism. In one particular embodiment of the present invention, DNA within a microorganism may be stained using Vybrant® DyeCycle™. Other DNA stains are well known and available. Indeed the number of stains available in the art for staining bacteria is vast and large numbers of such stains have been documented, including in standard reference texts, and are commercially available, e.g. from Life Technologies. Direct labelling of microorganisms by staining is easy to perform, convenient and cost-effective, and therefore represents a preferred embodiment.

Thus for example, the microorganisms may be grown for the AST test in wells of a microtiter plate, and the end of the growth periods the dye or stain may be added and the plate wells may be imaged and the number or amount of microorganisms may be assessed, by determining the number and/or size of microbial cells, aggregates or colonies e.g. by counting or imaging. Alternatively, microorganisms may be enumerated using a flow cytometer or similar type of instrument, for example the Aquila 400 instrument from Q-linea AB (Sweden), e.g. as described in U.S. patent application No. 61/979,319.

In an alternative embodiment a microorganism may be specifically labelled via a biological feature within or on the microorganism. A "biological feature" may for example be a molecule in or on the microorganism e.g. a protein or other biomolecule expressed or located on the cell surface. For example a label, e.g. a coloured or fluorescent label, may be coupled to a protein or other affinity binding molecule that binds specifically to a particular biological feature. In one embodiment the protein may be a lectin, affibody or antibody, or antibody fragment. The microorganisms labelled in this way may be detected e.g. enumerated as previously described.

In a further embodiment proximity probes may be used to detect a specific biological feature within or on a microorganism.

In a further alternative embodiment of the present invention the microorganisms may be detected and enumerated using the padlock probe and RCA-based amplified single molecule detection (ASMD) method discussed above (for use in the molecular tests). Such methods enable single microbial cells to be detected and counted. Thus, the microorganism may be detected by binding of the padlock probe and the number of microorganisms in a sample may be measured indirectly by an amplified signal generated via RCA of the circularised padlock probe. Each RCA product (blob) may be indicative of a single microorganism. Microorganisms may be lysed and padlock probes may be used which are designed to hybridise to one or more nucleotide sequences of the microorganisms. This may include a step of separating DNA as discussed above, and preferably of selectively separating, or enriching for, microbial DNA, again as discussed above. Since in the AST test the cultures are usually less complex than in the step of initial clinical sample culture, a simplified protocol for separating or enriching microbial DNA may be used, involving for example filtration to separate microorganisms and microbial cell lysis or simply direct microbial cell lysis.

Alternatively, affinity binding molecules may be used which bind to one or more molecules present on a microorganism or within a lysed microorganism, such an affinity probe being provided with an nucleic acid label or tag to which a padlock probe may hybridise i.e. akin to an immunoRCA detection procedure. Similarly proximity probes may be used to bind to a target in or on a microorganism and the nucleic acid domains of the proximity probes may be used to template the ligation of a padlock probe and optionally also prime its amplification by RCA. Procedures for this are widely known and described in the literature. As above C2CA may be used for signal amplification. The number of microorganisms in a sample can therefore be estimated by counting the number of blobs, which may be labelled e.g. fluorescently-labelled as described above 'blobs' within a sample. This thus provides another convenient means of obtaining a digital phenotypic susceptibility readout.

It is generally speaking advantageous in performing an AST test for the microbial culture under test to be pure, i.e. for there to be a single microorganism. Thus, in a preferred embodiment, in step (f), the AST test is performed if a single microorganism is identified in the nucleic acid tests of step (e). That is, the AST test of step (f) is performed if the clinical sample is determined to contain only a single microorganism. This ensures that only a pure culture may be used in the AST test. Thus in certain embodiments if two or more microorganisms are identified, the AST step of step (f) is not performed and the method continues as in step (g). However, this is not an essential feature, and it is possible to use microbial detection methods based on visualisation or imaging to perform AST tests, for example methods as provided by Accelerate Diagnostics which use imaging of bacteria on a surface and not in solution, or indeed methods in which labelled microorganisms are detected in fluidic systems e.g. the automated microscopy fluidic cassette-based systems of Price et al. 2014, J. Microbiol. Met. 98, 50-58 and by Metzger et al., 2014. J. Microbiol. Met. 79, 160-165, discussed above. Any cell-by-cell detection and identification methods may be used for AST testing of samples which contain more than one microorganism.

Conveniently the methods of the invention may be automated. Any one of more of the steps may be automated, preferably any or all of steps (a) to (f). Various specific or preferred steps discussed above lend themselves well to automation, for example the preferred padlock probe based ASMD methods for molecular testing and/or AST testing and the microbial/colony counting methods. Automatic culturing methods have already been developed, including for blood culture methods for microbial identification and/or AST testing and can be used or adapted for use according to the present invention. Automation would provide the advantage of speed and ease of operation, as well as multiplexing ability, which are of importance in clinical laboratory setting and especially important in the diagnosis of sepsis.

Viewed from a further aspect, the invention provides a microorganism detection device for detecting and characterising a microorganism in a clinical sample, said device comprising:

a first culture vessel containing a culture medium and being arranged to hold the clinical sample;

optionally a second culture vessel containing a culture medium;

optionally a portion removal device for removing a portion of the contents of the first culture vessel and transferring the portion to the second culture vessel;

wherein the first culture vessel is for culturing the clinical sample;

and wherein the second culture vessel is arranged to receive a clinical sample/medium mixture or a clinical sample culture as the portion of the contents of the first culture vessel, and is arranged to culture the portion, the device further comprising:

a test aliquot extraction device for removing a portion of the contents of the first and/or second culture vessel for use as a test aliquot; and a DNA testing device for separating DNA from said test aliquot, and performing nucleic acid tests on said DNA to identify the microorganism and to detect the presence or absence of one or more genetic antimicrobial resistance markers in said microorganism, wherein the DNA testing device is arranged to perform the nucleic acid tests using:

i. one or more nucleic acid probes or primers for microbial identification, a said probe or primer being capable of hybridising specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridising to, or a said primer being capable of selectively amplifying, a nucleotide sequence representing a genetic antimicrobial resistance marker;

and it is detected whether or not said probes or primers have hybridised to said DNA and/or whether or not said primers have taken part in an amplification reaction;

wherein the microorganism detection device is arranged such that: if the given microorganism is identified by the DNA testing device, then the cultured clinical sample and/or cultured portion produced by the first and/or second culture vessel by culturing after extraction of the test aliquot is passed to an antimicrobial susceptibility test device for performing antimicrobial susceptibility test on said cultured clinical sample and/or cultured portion by monitoring microbial growth by assessing growth or markers for growth, and wherein the type and concentration of antimicrobial agents used in said antimicrobial susceptibility test is determined by the identity of the microorganism and antimicrobial resistance markers detected by the DNA testing device; and if the given microorganism is not identified by the DNA testing device, then the microorganism detection device further cultures said clinical sample and/or cultured portion in the first and/or second culture vessel to enable further microbial identification and antimicrobial susceptibility tests to be performed after additional culturing in order to identify the microorganism and determine its antimicrobial resistance profile.

Viewed from a further aspect, the invention provides a microorganism detection device for detecting and characterising a microorganism in a clinical sample, said device comprising: a culture vessel containing a culture medium and being arranged to hold the clinical sample; a test aliquot extraction device for removing a portion of the contents of the culture vessel for use as a test aliquot; wherein the culture vessel is for culturing the clinical sample after extraction of the test aliquot, and optionally before extraction of the test aliquot; a DNA testing device for separating DNA from said test aliquot, and performing nucleic acid tests on said DNA to identify the microorganism and to detect the presence or absence of one or more genetic antimicrobial resistance markers in said microorganism, wherein the DNA testing device is arranged to perform the nucleic acid tests using:

i. one or more nucleic acid probes or primers for microbial identification, a said probe or primer being capable of hybridising specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridising to, or a said primer being capable of selectively amplifying, a nucleotide sequence representing a genetic antimicrobial resistance marker;

and it is detected whether or not said probes or primers have hybridised to said DNA and/or whether or not said primers have taken part in an amplification reaction;

wherein the microorganism detection device is arranged such that: if the given microorganism is identified by the DNA testing device, then the cultured clinical sample produced by the culture vessel by culturing after extraction of the test aliquot is passed to an antimicrobial susceptibility test device for performing antimicrobial susceptibility test on said cultured clinical sample by monitoring microbial growth by assessing growth or markers for growth, and wherein the type and concentration of antimicrobial agents used in said antimicrobial susceptibility test is determined by the identity of the microorganism and antimicrobial resistance markers detected by the DNA testing device; and if the given microorganism is not identified by the DNA testing device, then the microorganism detection device further cultures said clinical sample in the culture vessel to enable further microbial identification and antimicrobial susceptibility tests to be performed after additional culturing in order to identify the microorganism and determine its antimicrobial resistance profile.

Viewed from a further aspect, the invention provides a microorganism detection device for detecting and characterising a microorganism in a clinical sample, said device comprising:

a first culture vessel containing a culture medium and being arranged to hold the clinical sample;

a second culture vessel containing a culture medium;

a portion removal device for removing a portion of the contents of the first culture vessel and transferring the portion to the second culture vessel;

wherein the first culture vessel is for culturing the clinical sample;

and wherein the second culture vessel is arranged to receive a clinical sample/medium mixture or a clinical sample culture as the portion of the contents of the first culture vessel, and is arranged to culture the portion;

the device further comprising:

a test aliquot extraction device for removing a portion of the contents of the second culture vessel for use as a test aliquot; and a DNA testing device for separating DNA from said test aliquot, and performing nucleic acid tests on said DNA to identify the microorganism and to detect the presence or absence of one or more genetic antimicrobial resistance markers in said microorganism, wherein the DNA testing device is arranged to perform the nucleic acid tests using:

i. one or more nucleic acid probes or primers for microbial identification, a said probe or primer being capable of hybridising specifically to, or a said primer being capable of selectively amplifying, a nucleotide sequence which is identificatory of a given microorganism; and ii. one or more nucleic acid probes or primers for antimicrobial resistance marker detection, a said probe or primer being capable of hybridising to, or a said primer being capable of selectively amplifying, a nucleotide sequence representing a genetic antimicrobial resistance marker;

and it is detected whether or not said probes or primers have hybridised to said DNA and/or whether or not said primers have taken part in an amplification reaction;

wherein the microorganism detection device is arranged such that: if the given microorganism is identified by the DNA testing device, then the cultured portion produced by the second culture vessel by culturing after extraction of the test aliquot is passed to an antimicrobial susceptibility test device for performing antimicrobial susceptibility test on said cultured portion by monitoring microbial growth by assessing growth or markers for growth, and wherein the type and concentration of antimicrobial agents used in said antimicrobial susceptibility test is determined by the identity of the microorganism and antimicrobial resistance markers detected by the DNA testing device;

and if the given microorganism is not identified by the DNA testing device, then the microorganism detection device further cultures said clinical sample and/or cultured portion in the first and/or second culture vessel to enable further microbial identification and antimicrobial susceptibility tests to be performed after additional culturing in order to identify the microorganism and determine its antimicrobial resistance profile.

In each of the foregoing three aspects, the microorganism detection device may be arranged to perform any or all of the method steps and preferred/optional steps set out above. Thus, the DNA testing device may be arranged to carry out any or all of the DNA testing steps described above, and the antimicrobial susceptibility test device may be arranged to carry out any or all of the antimicrobial susceptibility testing steps described above.

The apparatus may comprise a means for determining the amount of microbial cell matter (that is microbial biomass) present in a sample, particularly by assessing or determining this directly. This may be achieved by determining the amount of microbial biomass visually, and especially by imaging. Therefore, the apparatus may comprise an imaging means (for example a microscope and optionally a camera) for obtaining 2D images. The apparatus may comprise a processor for processing the images to determine the amount of microbial cell matter. The processor may be configured to determine the area of microbial biomass (more particularly the area of microbial biomass in the field of view under investigation, e.g in an image).

More generally, the imaging means and processor may be configured to determine the amount and/or number and/or size of microorganisms and/or microbial colonies or aggregates. This may include counting of cells or colonies, but is not limited to such methods and includes any means of visually assessing the amount of microbial growth by assessing (or determining) the size, area, shape, morphology and/or number of microbial cells, colonies or aggregates (the term "aggregate" includes any collection of cells in physical proximity e.g. a clump or cluster; this may include non-clonal clumps/clusters of cells which have aggregated or stuck together (e.g. neighbouring cells which have become aggregated) as well as clonal colonies). The parameter used to measure microbial growth may, but need not, vary according to the identity of the microbe (determined in step (e)) and the antimicrobial agents used in step (f). Indeed, depending on the organism and the antimicrobial agents used, the morphology or growth pattern of the cells may be affected, and this may be altered or changed from the "normal" or "typical" morphology or growth pattern, e.g. in the absence of the antimicrobial agent. Whilst some AST growth monitoring methods may depend on detecting such changes, it is not essential according to the present invention to take such changes into account and the amount (e.g area) of microbial growth or biomass may be determined irrespective of morphology and/or growth pattern. Thus the same growth monitoring method may be used regardless of the microbial cell and/or antimicrobial agents used.

The culture medium may be added to the first and/or second culture vessel(s) prior to operation of the device, or the first and/or second culture vessel may be filled with the culture medium when it is supplied. Typically the first and/or second culture vessel will be a consumable item. The clinical sample may be added to the first culture vessel whilst it is in the microorganism detection device, or it may be added to the vessel outside of the device before the vessel is inserted into the microorganism detection device. The first culture vessel may be arranged to receive the clinical sample, and this may occur before, after or at the same time as the culture medium is introduced into the culture vessel.

The first and/or second culture vessel may be any suitable type of vessel for handling the clinical sample of interest. In one example the clinical sample is a blood sample. For blood samples the blood may be drawn from a patient into a culture vessel outside the microorganism detection device and then the first culture vessel containing the sample and culture medium may be inserted into the microorganism detection device.

The further culturing of the clinical sample or portion in the first and/or second culture vessel may occur in the same piece of apparatus as the earlier testing steps, or alternatively the first and/or second culture vessel may be passed to a separate apparatus, with the microorganism detection device hence including multiple separate parts. In the latter case first and/or second culture vessel may be handled in such way during extraction that it can be cultured during the further culturing step in another dedicated apparatus, which may advantageously be an apparatus that is already in place at the facility in question, which may for example be a hospital. Thus the first and/or second culture vessel is made available for continued culturing and this may be inside the same apparatus as the preceding steps, or outside that apparatus and in another separate part of the device.

The invention will now be described in more detail in the Examples below with reference to the following drawings in which:

FIG. 1 depicts in (A) a sample microarray panel for the detection of microorganisms in a sample, and in (B) the fluorescence intensity of the signal generated for a range of microorganisms. In FIG. 1A, the spots at the four corners and in the middle of the left hand side of the image are reference spots used for image alignment. The three brighter spots indicate that nucleotide sequences specific for *E. coli* are detected in the sample using the detection method of the present invention. FIG. 1B shows the signal generated for a range of different microorganisms when probes specific for *E. coli* are used, and indicates that the method of the present invention is capable of detecting the presence of a specific microorganism—in this case *E. coli*—in a sample.

Figure 2:
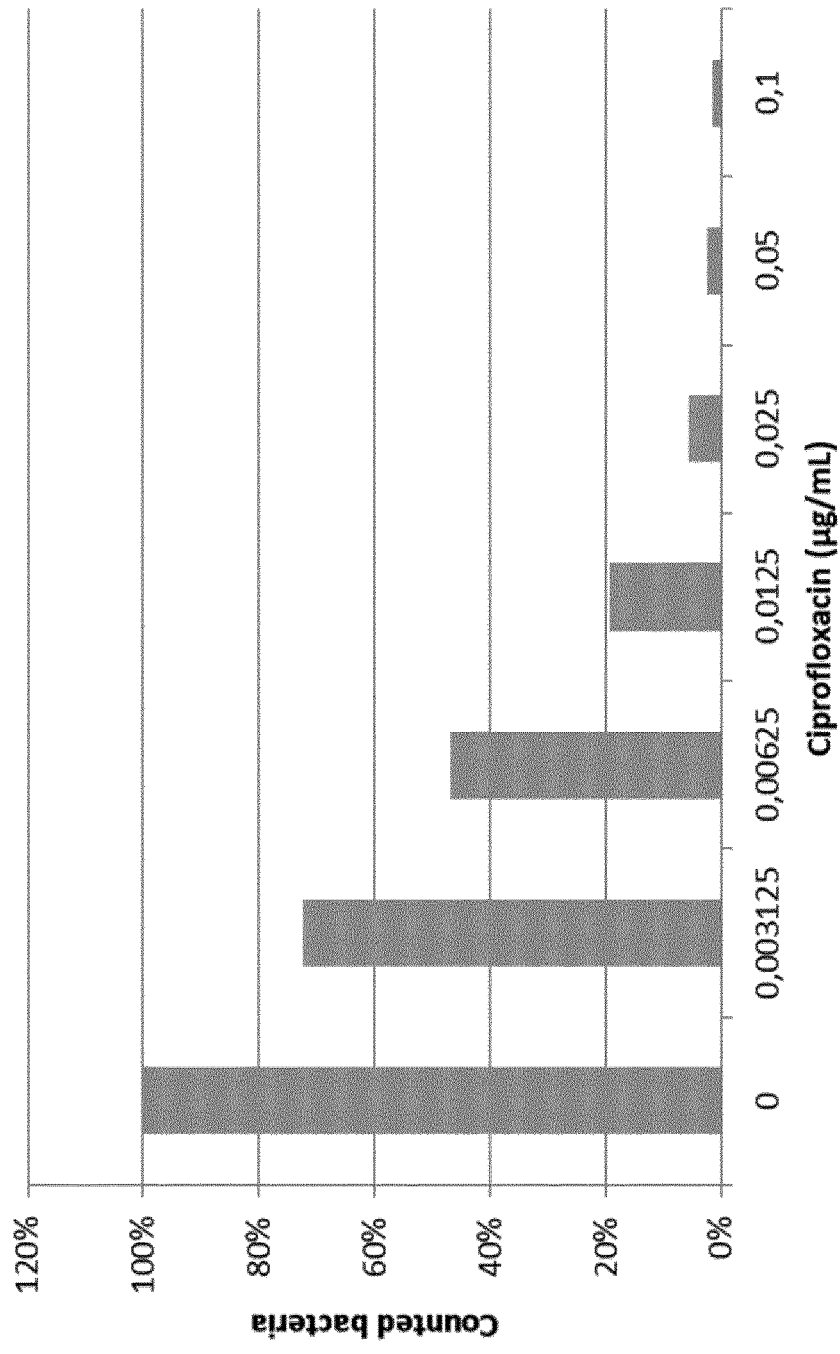

FIG. 2 shows the relative growth of bacteria grown in MH broth supplemented with ciprofloxacin at a range of different concentrations, relative to a positive control sample grown in the absence of ciprofloxacin. Cells were stained with Vybrant® DyeCycle™ Orange stain and counted by automated microscopy.

Figure 3:
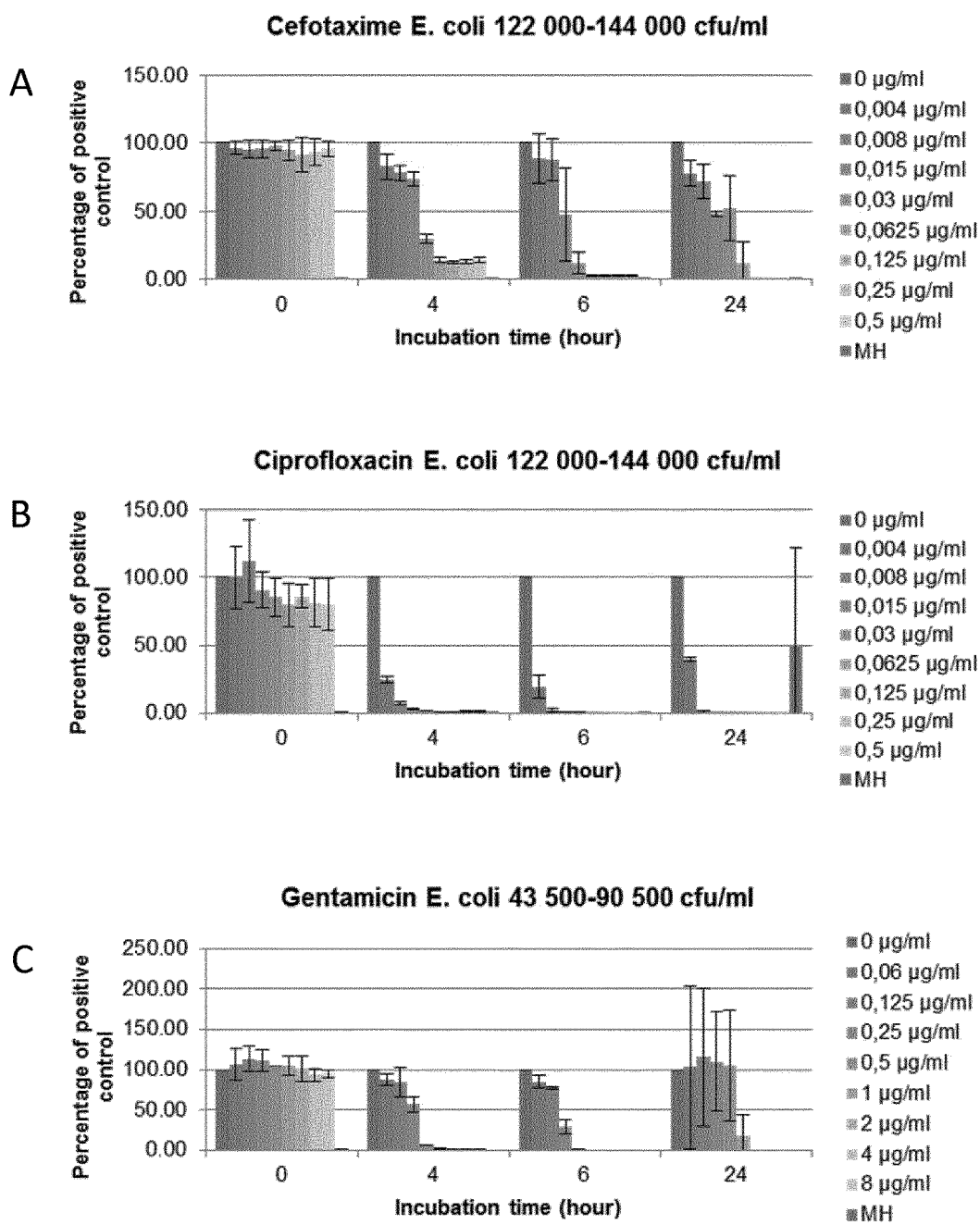
Figure 3:
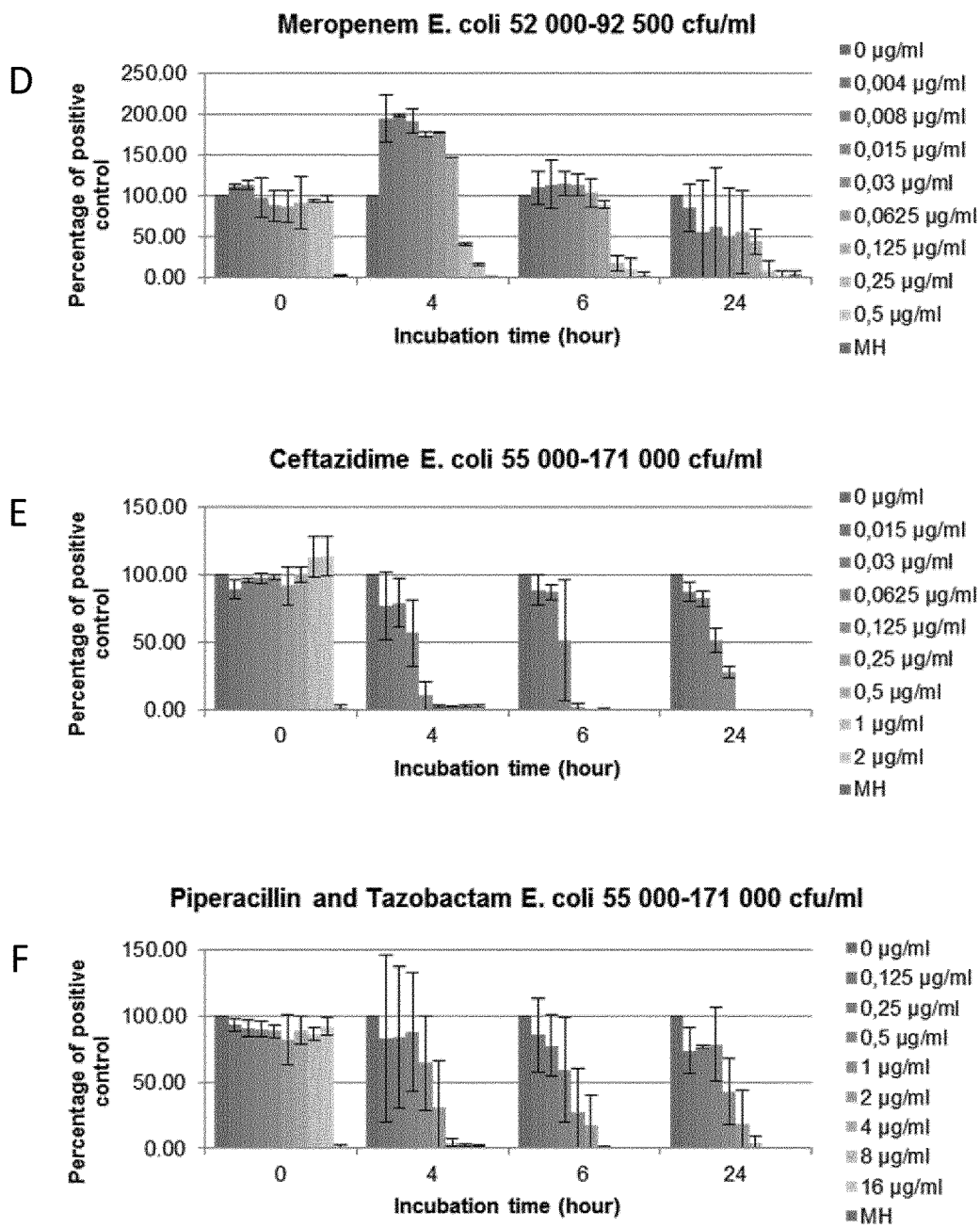

FIG. 3 shows the relative growth of bacteria grown in MH broth supplemented with a number of different antibiotics, each at a range of different concentrations, relative to positive control samples grown in the absence of any antibiotics (A—Cefotaxime, B—Ciprofloxacin, C—Gentamicin, D—Meropenem, E—Ceftazidime, F—Piperacillin+Tazobactam). Cells were stained with Vybrant® DyeCycle™ Orange stain and counted by Aquila 400. These data indicate that differential growth can be detected within 4 hours. MIC values were calculated for each of the antibiotics at 4, 6 and 24 hours, and at a range of cut-off values.

Figure 4:
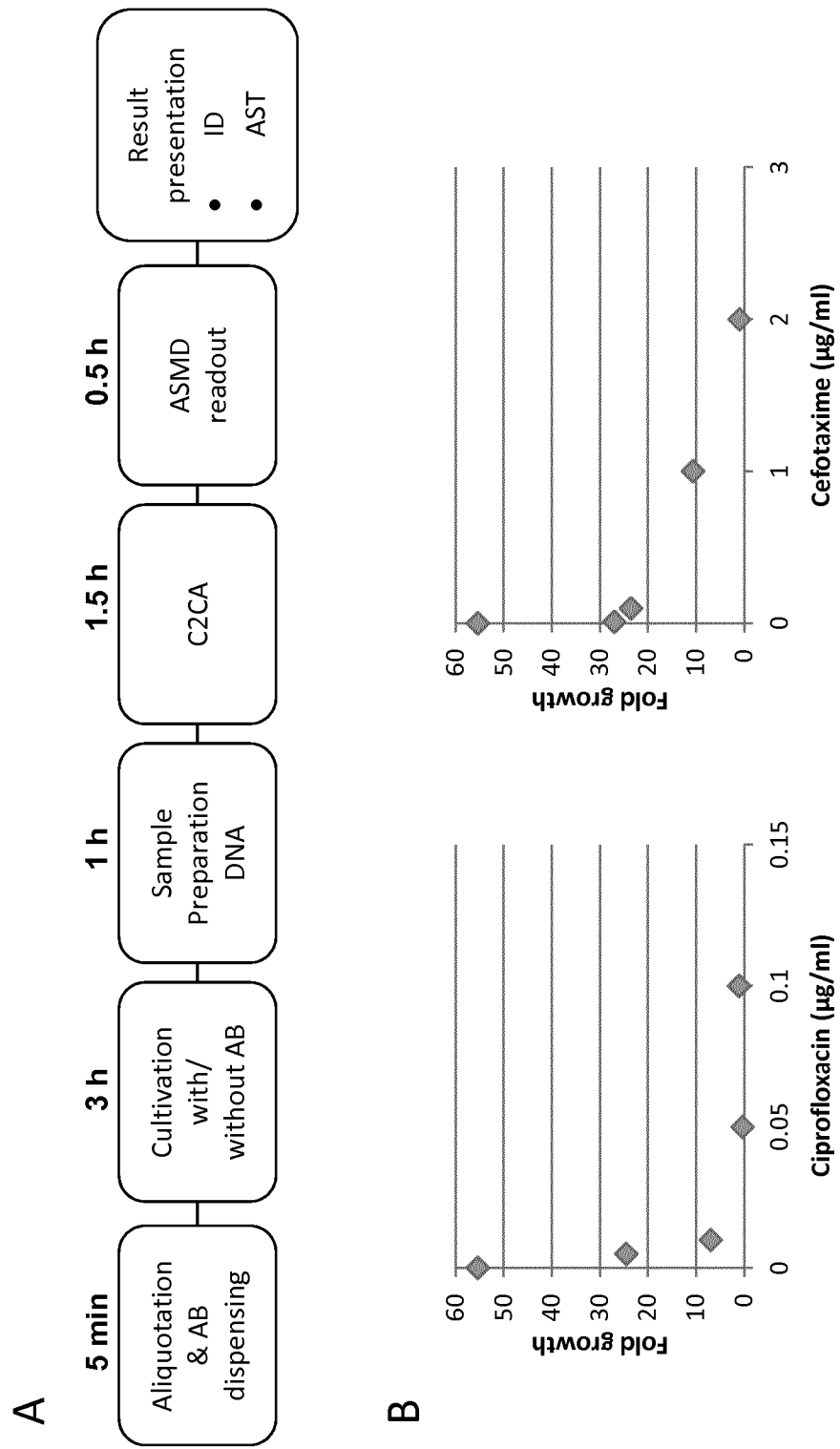

FIG. 4 depicts in (A) the workflow required for Amplified Single Molecule Detection (ASMD) of bacteria within a sample to determine antibiotic susceptibility of a microorganism, and in (B) shows the differential growth of bacteria grown in MH broth supplemented with Ciprofloxacin or Cefotaxime, relative to a positive control sample grown in the absence of either antibiotic. In FIG. 4B, the RCA products indicating the presence of specific microbial DNA sequences are detected by ASMD, and counted by Aquila 400.

Figure 5:
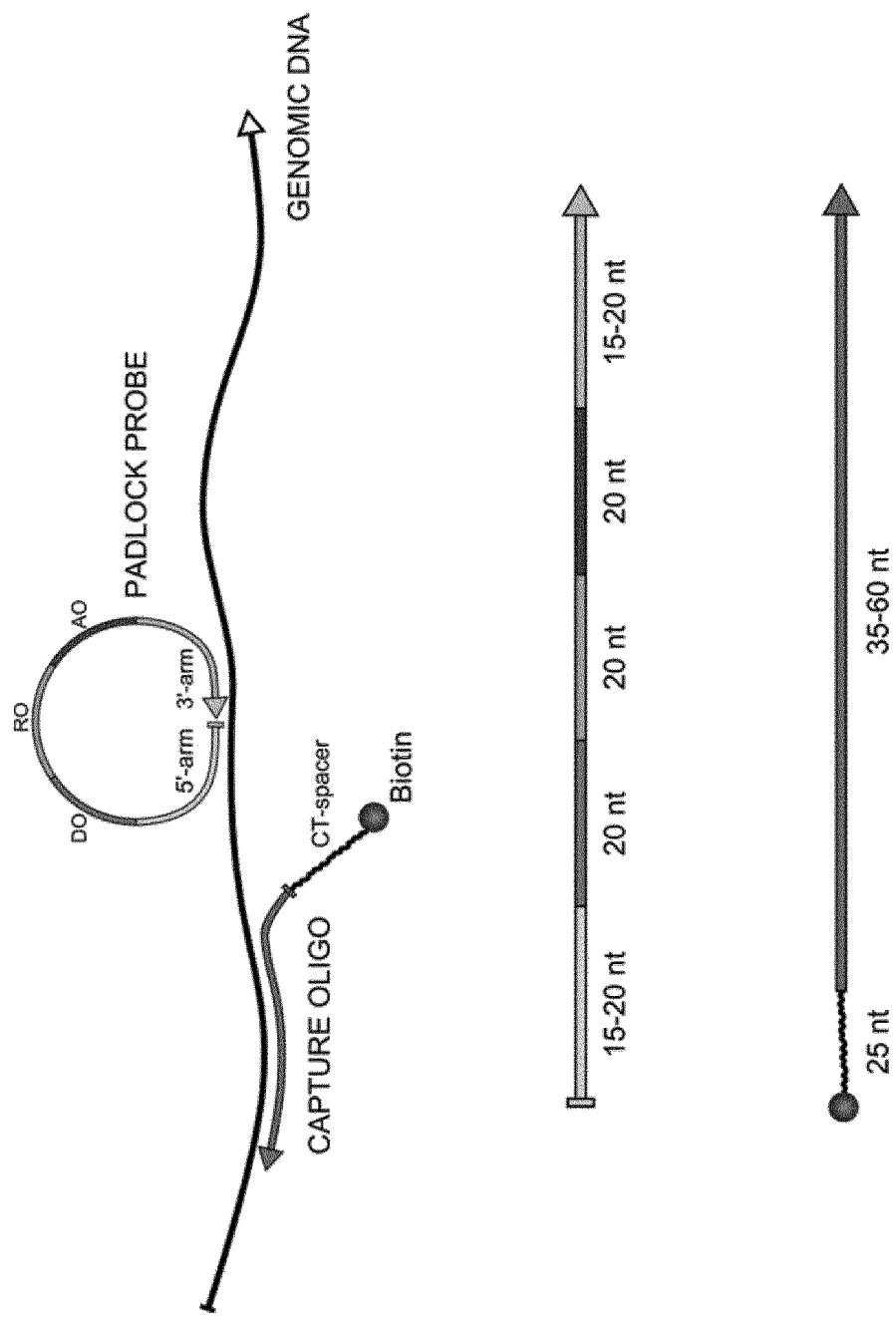

FIG. 5 depicts a scheme for detecting specific microbial DNA sequences for use in probe design. A biotinylated capture oligonucleotide complementary to a region of microbial DNA binds a target DNA fragment and immobilises it onto a solid phase. A padlock probe, comprising two target-complementary parts (5'/3'-arms) and a backbone with sites for detection (DO—generic), restriction digestion and priming (RO—generic), and array oligo hybridization (AO—unique) binds to its target via its complementary 5' and 3' end sequences, and can be ligated into a circle prior to RCA amplification and C2CA reaction.

Figure 6:
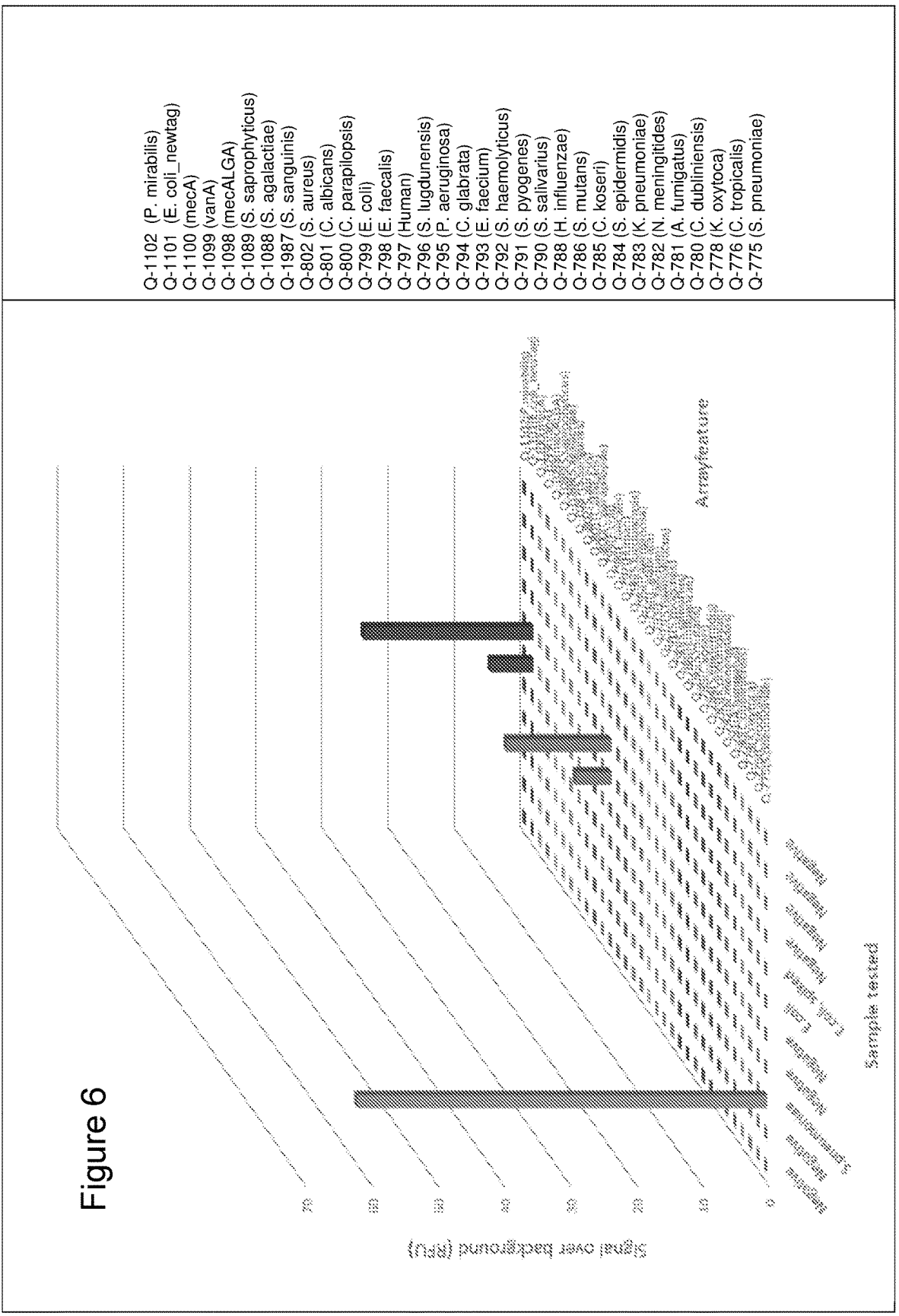

FIG. 6 presents the results of the experiment in Example 6 to detect microorganisms in 10 clinical samples and 1 spiked sample, and shows the fluorescent signals detected (RFU, relative fluorescent units) on a microarray when probes specific for different bacteria were used. 8 of the clinical samples were found to be negative, one clinical sample was found to contain *E.coli*, one clinical sample was found to contain *S. pneumonia*, and the sample spiked with *E.coli* was found to contain *E.coli*, showing that specific microorganisms can be detected in clinical samples; and FIG. 7 presents the results of the experiment in Example 7 and shows the time taken to obtain a positive blood culture result (TPP, time to positivity) for sets of blood culture flasks (BCFs) spiked with 50,000 CFU/ml and 500 CFU/ml blood in the BCF respectively at the time of sampling. TPP was found not to differ significantly between the set.

EXAMPLES

Example 1—Blood Culture and Microbial Identification and Characterisation by Molecular Tests Blood spiked with 500 µl of *E. coli* bacterial suspension to give a concentration of $10^3$ CFU/ml was added to a BacT/ALERT FA plus (Biomerieux) blood culture flask with a needle through the septa. For pre-culture we used an own designed Multirotators from Grant Instruments (Grant-bio PTR-35) re-designed to blood culture flask (BCF) agitators. Samples were incubated for 4 hours at 35° C.

5 ml of the sample was aspirated, equivalent to 1 ml of whole blood, using a syringe. Enrichment of bacterial DNA was carried out by the method from Molzym (Germany) without the need for centrifugation.

Preparation of lysis buffer by addition of 800 µl ES to 160 µl MoIDNase. Mix by pipetting 6× and add all of the MoIDNase solution to 12800 µl lysis buffer followed by mix by pipetting 6×.

Preparation of Proteinase K. Add 1000 µl ES to 400 µl Proteinase K and mix by pipetting 6×.

Lysis

Add 5 ml sample withdrawn from the BCF to 4300 µl Lysis-MoIDNase buffer and mix by pipetting 8×. Incubate at 45° C. for 10 min.

Inactivating MoIDNase and add 350 µl Proteinase K to the lysate and mix by pipetting 8×.

Incubate at 45° C. for 10 min.

Sample Capture to Column and Wash, 3 Loops

Add 605 µl lysate to a filter column (Molzym, Germany), apply 15 seconds vacuum. Add 500 µl RS to the filter column and apply 15 seconds vacuum. Add 605 µl lysate to a filter column (Molzym, Germany), apply 30 seconds vacuum. Add 500 µl RS to the filter column and apply 15 seconds vacuum. Add 605 µl lysate to a filter column (Molzym, Germany), apply 45 seconds vacuum. Add 500 µl RS to the filter column and apply 15 seconds vacuum. Continue with 45 seconds vacuum after sample addition until all sample have been added. More than one filter may be used in order to filter the lysate, if required, if the filter becomes clogged during filtration.

Preparation of Lysis Buffer for Microbes

Add 5.6 µl β-mercaptoethanol to 600 µl RL and mix by pipetting 6×, Add all pre-mixed BM-RL to 80 µl BugLysis and mix by pipetting 6×

Lysis of Microbes

Add 170 µl of the prepared lysis mixture to the column and apply vacuum for 200 ms. Incubate at 45° C. for 10 min. Add 280 µl prepared Proteinase K-solution to 520 µl Buffer RP. Mix by pipetting 6×. Add 200 µl PK-RP to column. Apply vacuum for 200 ms. Incubate at 45° C. for 10 min Binding of Microbial DNA to Column Move column to room tempered block. Wait for 2 minutes. Add 500 µl CSAB to column. Apply vacuum for 2 s.

Wash 1
Add 500 µl WB to column. Apply vacuum for 2 s.
Wash 2
Add 500 µl WS to column. Apply vacuum for 2 s.
Drying of membrane
Apply vacuum for 10 min
Elution
Add 200 µl ET to column
Apply vacuum for 200 ms.
Incubate at RT for at least 5 min
Apply vacuum for 1 min
Repeat once to make two elutions.

The molecular test was carried out on the enriched bacterial DNA sample by the method in Göransson et al, 2012 (supra). During the process of molecular identification of the bacteria the remaining blood sample was kept under agitators.

Padlock probes and target capture probes were ordered from Integrated DNA Technologies (Munich, Germany). The probes were designed to detect unique motifs in each bacteria, selected via bioinformatics tools. The hybridization of capture probes and ligation of padlock probes to the target DNA were performed simultaneously, and was achieved by incubating fragmented and denatured genomic DNA in 20 mM Tris-HCl (pH 8.3), 25 mM KCl, 10 mM MgCl2, 0.5 mM NAD, 0.01% Triton® X-100, 100 nM padlock probe, 50 nM capture probe, 0.2 µg/µl BSA (New England Biolabs, MA, USA), and 250 mU/µl Ampligase (Epicentre Biotechnologies, WI, USA) at 55° C. for 5 min. The target DNA along with reacted padlock probes were captured onto magnetic particles via the biotinylated capture probes. This was achieved by adding 50 µg Dynabeads MyOne™ Streptavidin T1 beads (Invitrogen) to the hybridization/ligation reaction and incubating the sample at room temperature for 3 min. Excess probes were eliminated by washing once with 100 µl washing buffer containing 5 mM Tris-HCl (pH 7.5), 5 mM EDTA, 1 M NaCl, and 0.1% Tween-20. The elimination of excess linear padlock probes is performed, since these may otherwise interfere negatively with the subsequent RCA reaction.

Reacted probes were amplified by C2CA, which includes serial enzymatic reactions starting with RCA. The RCA reaction was initiated by the addition of 20 µl ligation mixture containing 1×phi29 DNA polymerase buffer (Fermentas, Lithuania; 33 mM Tris-acetate (pH 7.9 at 37° C.), 10 mM Mg-acetate, 66 mM K-acetate, 0.1% (v/v) Tween-20, 1 mM DTT), 100 µM dNTPs, 0.2 µg/µl BSA, 25 nM primer, and 100 mU/µl phi29 DNA polymerase. The reaction was incubated at 37° C. for 11 min, and inactivated at 65° C. for 1 min. The RCA products were digested at 37° C. for 1 min by the addition of 3 units of AluI (New England Biolabs), 600 nM replication oligonucleotide, 0.2 µg/µl BSA in 1×phi29 DNA polymerase buffer, and the reaction was terminated at 65° C. for 1 min. Ligation, amplification and labelling reactions were performed by the addition of a mixture containing 1.36 mM ATP, 100 µM dNTPs, 0.2 µg/µl BSA, 28 mU/µl T4 DNA ligase and 120 mU/µl phi29 DNA polymerase in 1×phi29 DNA polymerase buffer to a final volume of 50 µl. The reactions were incubated at 37° C. for 7 min, and terminated at 65° C. for 1 min. The above was repeated once. After the final RCA the products were digested once again into monomers. The RCPs were now ready for analysis.

The digested sample was transferred to a microarray, incubated at 55° C. for 30 minutes followed by a wash with 1×SSC in RT. The hybridized RCA monomers is then labelled via hybridization of a detector oligo at 10 nM concentration in 2×SSC at 55° C. for 30 minutes, washed twice in 1×SSC at RT and spun dry.

The array was then scanned in an array scanner and the result analysed using array image analysis software as follows.

The array image is evaluated in order to detect spots corresponding to one or several pathogens. A lit spot corresponds to a detected pathogen, with a redundancy of three spots per pathogen. Further, the array has reference spots used for image alignment, which are always lit, and protocol reference spots which—if lit—verify that the individual steps of the molecular protocol succeeded. The analysis is divided into the following steps:

1. The reference spots are detected and the image is aligned accordingly.
2. The spot intensities and backgrounds are measured and the background corrected values are calculated.
3. The measured intensities are compensated for pathogen specific background, such as e.g. unspecific binding of DNA from probe sets corresponding to other pathogens.
4. The array intensity data is used to provide an answer on pathogen id(s) and a quality value
   a. The algorithm takes the intensity value of all replicate spots corresponding to a specific pathogen into account when calculating the ID answer.
   b. The ID answer may be qualitative (reporting presence of pathogen), and/or quantitative (reporting an indication of the amount of pathogen present in the sample)
   c. The protocol reference spots are evaluated in order to verify that the molecular protocol succeeded.
5. The result is collected and may be transferred to downstream AST analysis and/or reported out in a result report. The result includes:
   a. The ID of the detected pathogen(s)
   b. Semi quantitative values for each detected pathogen
   c. A quality value indicating the success rate of the molecular protocol.

A sample array image is shown in FIG. 1A. The five spots along the edges of the plate are reference spots and are used for image alignment. Brighter spots indicate a detected pathogen (*E. coli*). FIG. 1B shows that a fluorescent signal was specifically generated for *E. coli*.

Example 2—AST Testing on the Blood Culture of Example 1

5 ml from the remaining sample in the blood culture bottle, that had continued to be under culture conditions during the molecular typing, was drawn from the flask.

The drawn sample was enriched for bacteria and at the same time the culture media was changed, in this case to Mueller-Hinton media (MH-media). *E. coli* bacteria were recovered via filtration through a 0.2 µm filter and then the recovered bacteria were resuspended in MH-media. 63 µl aliquots of the bacterial suspension were transferred to selected wells in a microtiterplate.

Each well had a different concentration of antibiotics as well as different antibiotics. As the microorganism identified in Example 1 was *E. coli* in this case, the following antibiotics were selected for use in antimicrobial susceptibility testing: Ciprofloxacin, Piperacillin+Tazobactam, Cefotaxime, Ceftazidim, Meropenem and Gentamicin. A series of six different concentrations was prepared for each antibiotic based on known clinical MIC values. A seventh well containing MH broth and no antibiotic was used as a positive control. The microtiterplate was incubated at 35° C. for 4 hours before the plate was read. 7 µl 10 µM Vybrant®

DyeCycle™ Orange stain (Molecular Probes® Life Technologies) was added to each well and incubated for 30 min at 37° C. Each microtiterplate well was imaged and the number of bacteria were counted. The differential growth relative to the positive control was used to determine a MIC value for the bacteria. The result for Ciprofloxacin is shown in FIG. 2.

Example 3—Determination of AST Profiles Using Counting of Individual Bacteria in a Flow Cytometry Type Instrument (Aquila 400, Q-Linea AB, Sweden)

Bacteria were grown in blood culture as described in Example 1. 5 ml from the remaining sample in the blood culture bottle, that had continued to be under culture conditions during the molecular typing, was drawn from the flask.

The sample was enriched for bacteria and at the same time the culture media was changed, in this case to Mueller-Hinton media (MH-media). *E. coli* bacteria were recovered via filtration through a 0.2 μm filter and the recovered bacteria were resuspended in MH-media to a concentration of approximately $10^8$ CFU/ml in Müller Hinton broth before being diluted to approximately $10^6$ CFU/ml in Müller Hinton Broth.

Antibiotic solutions were prepared in a series of 2:1 serial dilutions in Müller Hinton broth at 10× test concentrations. The range of antibiotic concentrations was chosen based on identity of the bacteria and the antibiotic. As the microorganism identified in Example 1 was *E. coli* in this case the following antibiotics were selected for use in the antimicrobial susceptibility test: Ciprofloxacin, Piperacillin+Tazobactam, Cefotaxime, Ceftazidim, Meropenem and Gentamicin. A series of eight different concentrations was selected based on known clinical MIC values. Eight sample tubes containing 100 μl antibiotic solution at eight different concentrations and 800 μl Müller Hinton broth were prepared. One additional tube contains 900 μl Müller Hinton broth and no antibiotic as positive control. 100 μl bacterial suspension ($10^6$ CFU/ml) was added to all nine tubes. A negative control sample comprising 1000 μl Müller Hinton broth (i.e. no bacteria) is prepared as negative control.

All tubes were incubated at 35° C. and samples were taken after 0, 4, 6 and 24 hours. Bacterial samples were prepared for counting as in Example 2. Bacterial AST profiles were determined using a flow cytometry based counting of individual bacteria in an Aquila 400 instrument (Q-linea AB, Sweden). Aquila 400 analysis was performed using the alexa 488 laser.

It was evident from the analysis performed at different time points that 4 hours was sufficient for detecting differential bacterial growth at the different concentration of antibiotics and thus to determine antibiotic susceptibility. Shorter times have been shown in the literature so this is not unexpected. Differential bacterial growth relative to the positive control sample for each antibiotic is shown in FIG. 3. MIC values for each antibiotic at different time points and cut-off values were calculated based on the differential bacterial growth. Values obtained by this method compared favourably with previously reported clinical MIC values and are shown below. The results show excellent precision and sensitivity obtained by counting individual bacteria instead of averaging measurements.

Cefotaxime
MIC with Macrobroth dilution is 0.125 μg/ml and another lab has determined MIC with E-test to ≤0.5 μg/ml.

| Cut-off | 4 hours | 6 hours | 24 hours |
| --- | --- | --- | --- |
| 5% | — | 0.06 | 0.125 |
| 10% | — | 0.06 | 0.125 |
| 15% | 0.06 | 0.03 | 0.06 |
| 20% | 0.06 | 0.03 | 0.06 |

Ciprofloxacin
MIC with Macrobroth dilution is 0.016 μg/ml and another lab has determined MIC with E-test to ≤0.03 μg/ml.

| Cut-off | 4 hours | 6 hours | 24 hours |
| --- | --- | --- | --- |
| 5% | 0.016 | 0.008 | 0.008 |
| 10% | 0.008 | 0.008 | 0.008 |
| 15% | 0.008 | 0.008 | 0.008 |
| 20% | 0.008 | 0.004 | 0.008 |

Gentamicin
MIC with Macrobroth dilution is 0.5-1 μg/ml and another lab has determined MIC with E-test to 1 μg/ml.

| Cut-off | 4 hours | 6 hours | 24 hours |
| --- | --- | --- | --- |
| 5% | 1 | 0.5 | 1 |
| 10% | 0.5 | 0.5 | 1 |
| 15% | 0.5 | 0.5 | 1 |
| 20% | 0.5 | 0.5 | 1 |

Meropenem
MIC with Macrobroth dilution is 0.25-0.5 μg/ml and another lab has determined MIC with E-test to ≤0.25 μg/ml. MIC estimated with Macrobroth dilution and with Aquila 400 is too high because old stock of antibiotics was used.

| Cut-off | 4 hours | 6 hours | 24 hours |
| --- | --- | --- | --- |
| 5% | — | — | 0.5 |
| 10% | — | — | 0.5 |
| 15% | — | 0.5 | 0.25 |
| 20% | 0.5 | 0.25 | 0.125 |

Ceftazidime
MIC with Macrobroth dilution is 0.25 μg/ml and another lab has determined MIC with E-test to ≤0.5 μg/ml.

| Cut-off | 4 hours | 6 hours | 24 hours |
| --- | --- | --- | --- |
| 5% | 0.25 | 0.125 | 0.25 |
| 10% | 0.25 | 0.125 | 0.25 |
| 15% | 0.125 | 0.125 | 0.25 |
| 20% | 0.125 | 0.125 | 0.25 |

Piperacillin and Tazobactam
MIC with Macrobroth dilution is 4-8 μg/ml and another lab has determined MIC with E-test to 2 μg/ml.

| Cut-off | 4 hours | 6 hours | 24 hours |
| --- | --- | --- | --- |
| 5% | 4 | 4 | 4 |
| 10% | 4 | 4 | 4 |

-continued

| Cut-off | 4 hours | 6 hours | 24 hours |
|---|---|---|---|
| 15% | 4 | 4 | 4 |
| 20% | 4 | 2 | 2 |

Example 4—Method with AST Determination by AST Using Padlock Probes and C2CA Amplification Blood cultures spiked with *E. coli* were set up and molecular typing was performed as described in Example 1. 5 ml from the remaining sample in the blood culture bottle, that had continued to be under culture conditions during the molecular typing, was drawn from the flask and the sample was enriched for bacteria and changed into MH-media as in Example 2.

63 µl aliquots were transferred to selected wells in a microtiterplate. Each well had a different concentration of antibiotics as well as different antibiotics. In one microtiterplate 12 different antibiotics had been placed, each at four different concentrations and one blank, i.e. no antibiotics. After 4 hours growth in the microtiterplate each well were subjected to bacterial lysis to release the bacterial DNA.

Antibiotic susceptibility testing was performed using Amplified Single Molecule Detection (ASMD) where the DNA from pathogens is extracted followed by digital counting of amplification products, rather than by direct labelling of bacteria. The molecular detection test was carried out on the bacterial DNA sample by the method in Göransson et al, 2012. Padlock probes and target capture probes were ordered from Integrated DNA Technologies (Munich, Germany).

The probes were designed to detect unique motifs in each bacteria, selected via bioinformatics tools. the hybridization of capture probes and ligation of padlock probes to the target DNA were performed simultaneously, and was achieved by incubating fragmented and denatured genomic DNA in 20 mM Tris-HCl (pH 8.3), 25 mM KCl, 10 mM MgCl2, 0.5 mM NAD, 0.01% Triton® X-100, 100 nM padlock probe, 50 nM capture probe, 0.2 µg/µl BSA (New England Biolabs, MA, USA), and 250 mU/µl Ampligase (Epicentre Biotechnologies, WI, USA) at 55° C. for 5 min. The target DNA along with reacted padlock probes were captured onto magnetic particles via the biotinylated capture probes. This was achieved by adding 50 µg Dynabeads MyOne™ Streptavidin T1 beads (Invitrogen) to the hybridization/ligation reaction and incubating the sample at room temperature for 3 min. Excess probes were eliminated by washing once with 100 µl washing buffer containing 5 mM Tris-HCl (pH 7.5), 5 mM EDTA, 1 M NaCl, and 0.1% Tween-20. The elimination of excess linear padlock probes is necessary, since these would otherwise interfere negatively with the subsequent RCA reaction.

Reacted probes were amplified by C2CA, which includes serial enzymatic reactions starting with RCA. The RCA reaction was initiated by the addition of 20 µl ligation mixture containing 1×phi29 DNA polymerase buffer (Fermentas, Lithuania; 33 mM Tris-acetate (pH 7.9 at 37° C.), 10 mM Mg-acetate, 66 mM K-acetate, 0.1% (v/v) Tween-20, 1 mM DTT), 100 µM dNTPs, 0.2 µg/µl BSA, 25 nM primer, and 100 mU/µl phi29 DNA polymerase. The reaction was incubated at 37° C. for 11 min, and inactivated at 65° C. for 1 min. The RCA products were digested at 37° C. for 1 min by the addition of 3 units of AluI (New England Biolabs), 600 nM replication oligonucleotide, 0.2 µg/µl BSA in 1×phi29 DNA polymerase buffer, and the reaction was terminated at 65° C. for 1 min. Ligation, amplification and labelling reactions were performed by the addition of a mixture containing 1.36 mM ATP, 100 µM dNTPs, 0.2 µg/µl BSA, 28 mU/µl T4 DNA ligase and 120 mU/µl phi29 DNA polymerase in 1×phi29 DNA polymerase buffer to a final volume of 50 µl. The reactions were incubated at 37° C. for 7 min, and terminated at 65° C. for 1 min. The above was repeated once. After the last RCA reaction fluorescent labelled oligonucleotides complementary to the RCP was added at a concentration of 5 nM each. The reaction was incubated at 65° C. for 2 minutes followed by 5 minutes at 37° C. and allowed to cool down.

The samples were then injected into Aquila 400, (U.S. Patent Application No. 61/979,319) and number of RCP products were recorded as described in Jarvius et al, 2006 (Jarvius J., et al, Nature Methods 3, 725-727 (2006). The number of RCP products detected for the bacterial sample grown at each concentration of Ciprofloxacin and Cefotaxime is shown in FIG. 4. This data was used to estimate an MIC concentration for each antibiotic.

Example 5—Strategy for Probe Design

Identification of the pathogen can performed in multiplex. For this each included pathogen has up to three specific capture oligonucleotides used to fish out the target DNA. Each pathogen also has up to three specific padlock probes hybridizing to the target near to the respective capture oligonucleotides. The process for designing ASMD probe sets can be divided into two main steps: finding optimal target regions and designing the probe sequences.

Below is a further breakdown of the design process: Finding genomic targets—Acquire microbial genome sequences from a genome database (e.g. NCBI)—Partition genome sequences into target and background groups. —If more than one target genome, search for sequences common to all. —Apply a set of filters to remove low-complexity candidates (homopolymers, high/low %-GC, repeats, etc.)— Background filtering: candidates with high sequence similarity to genomes in background partition are discarded. —Report accepted candidates. Make probes—Load genomic targets to which probes will be designed (selected in the step above)—Choose settings (probe length, melting temperatures, hetero/homodimer filter, ligation filter, etc.)— Find optimal probe sequences. —Present passed candidates and a short design summary.

The probes used for filtering and recognition of genomic DNA targets are made up as shown in FIG. 5. The capture probe brings target fragments onto solid phase, and the padlock then binds to its target, gets ligated into a circle and is amplified in the subsequent C2CA reaction. The padlock has two target-complementary parts (5'/3'-arms) and a backbone with sites for detection (generic), restriction digestion and priming (generic), and array oligo hybridization (unique). The backbone parts are referred to as DO, RO, and AO in FIG. 5. The capture oligo consists of a target complementary part, a CT-linker and a biotin for attachment to solid phase.

Example 6—Blood Culture and Microbial Identification of Clinical Samples by Molecular Tests Blood from patients, at an ICU, with suspected sepsis were drawn into Bactec (Becton Dickinson) blood culture flask and cultured in a blood culture cabinet. After four hours of incubation, well before the flasks have indicated positively in the blood culture cabinet, a sample was drawn and used for molecular tests.

5 ml of the sample was aspirated, using a syringe and potential pathogen DNA was extracted as described in Example 1.

The molecular test was carried out on the enriched bacterial DNA sample by the method in Göransson et al, 2012 (supra).

Padlock probes and target capture probes were ordered from Integrated DNA Technologies (Munich, Germany). The probes were designed to detect unique motifs in each bacteria, selected via in-house developed bioinformatics tools. The hybridization of capture probes and ligation of padlock probes to the target DNA were performed simultaneously, and was achieved by incubating fragmented and denatured genomic DNA in 20 mM Tris-HCl (pH 8.3), 25 mM KCl, 10 mM MgCl2, 0.5 mM NAD, 0.01% Triton® X-100, 100 nM padlock probe, 50 nM capture probe, 0.2 µg/µl BSA (New England Biolabs, MA, USA), and 250 mU/µl Ampligase (Epicentre Biotechnologies, WI, USA) at 55° C. for 5 min. The target DNA along with reacted padlock probes were captured onto magnetic particles via the biotinylated capture probes. This was achieved by adding 50 µg Dynabeads MyOne™ Streptavidin T1 beads (Invitrogen) to the hybridization/ligation reaction and incubating the sample at room temperature for 3 min. Excess probes were eliminated by washing (once) with (100 µl) washing buffer containing 5 mM Tris-HCl (pH 7.5), 5 mM EDTA, 1 M NaCl, and 0.1% Tween-20. The elimination of excess linear padlock probes is performed, since these may otherwise interfere negatively with (the) subsequent RCA reaction.

Reacted probes were amplified by C2CA, which includes serial enzymatic reactions starting with RCA. The RCA reaction was initiated by the addition of 20 µl ligation mixture containing 1×phi29 DNA polymerase buffer (Fermentas, Lithuania; 33 mM Tris-acetate (pH 7.9 at 37° C.), 10 mM Mg-acetate, 66 mM K-acetate, 0.1% (v/v) Tween-20, 1 mM DTT), 100 µM dNTPs, 0.2 µg/µl BSA, 25 nM primer, and 100 mU/µl phi29 DNA polymerase. The reaction was incubated at 37° C. for 11 min, and inactivated at 65° C. for 1 min. The RCA products were digested at 37° C. for 1 min by the addition of 3 units of AluI (New England Biolabs), 600 nM replication oligonucleotide, 0.2 µg/µl BSA in 1×phi29 DNA polymerase buffer, and the reaction was terminated at 65° C. for 1 min. Ligation, amplification and labelling reactions were performed by the addition of a mixture containing 1.36 mM ATP, 100 µM dNTPs, 0.2 µg/µl BSA, 28 mU/µl T4 DNA ligase and 120 mU/µl phi29 DNA polymerase in 1×phi29 DNA polymerase buffer to a final volume of 50 µl. The reactions were incubated at 37° C. for 7 min, and terminated at 65° C. for 1 min. The above was repeated once. After the final RCA the products were digested once again into monomers. The RCPs were now ready for analysis.

The digested sample was transferred to vessel containing a microarray, incubated at 55° C. for 30 minutes followed by a wash with 1×SSC in RT. The hybridized RCA monomers is then labelled via hybridization of a detector oligo at 10 nM concentration in 2×SSC at 55° C. for 30 minutes, washed twice in 1×SSC at RT and spun dry.

The array was then scanned in an array scanner and the result analysed using image analysis software. The data shown have been normalized and only data are above background times 3 standard deviations from background are classified as true signals.

Data from 10 clinical samples plus one spiked sample is shown in FIG. 6. The spiked sample was spiked with *E. coli* into a blood culture flask with blood from a negative sample. The amount of bacteria spiked in corresponds to the amount that would have been present if the original amount were 10 CFU *E. coli*/ml blood into BCF and then grown for four hours. Eight of the clinical samples were found to be negative by blood culture, and two were found to be positive by blood culture. The positive samples were later identified as one *E. coli* and one *S. pneumoniae* using standard techniques.

The only positive signals obtained were from the expected array features for each sample. One of the clinical samples was found to contain *E. coli*, and one of the clinical samples was found to contain *S. pneumoniae* in this assay. The spiked sample was also confirmed to contain *E. coli*. No signal above background, defined as 3 times standard deviation of the average signal in a set of negative samples, was seen in any of the samples later confirmed to be negative using traditional confirmatory assays. For *E. coli* two array features per sample (Q1101 and Q799) gave rise to a signal, this is because two different probe systems both detecting *E. coli* but reporting on different array features were used in this experiment.

Example 7—Time to Positivity after Withdrawal of an Aliquot from the Blood Culture Flask 10 sets of blood culture flasks were spiked with bacteria. 5 sets were spiked with 500 CFU/ml blood and 5 sets were spike with 50.000 CFU/ml blood. 10 ml of blood from healthy donors were drawn per blood culture flask (with 30 ml blood culture medium) to give a total volume of 40 ml/culture flask. Before the blood culture flasks were put into the blood culture cabinet an aliquot of 5 ml were withdrawn. Every 30 minutes we controlled if the blood culture flasks have indicated positivity in the blood culture cabinet.

The time-to-positivity (TTP) is shown in FIG. 7, and was not found to differ significantly between the set. No significant difference was found between flasks that had an aliquot removed prior to culture, and flasks which did not have an aliquot removed.

Example 8—Aseptic Sampling of an Aliquot from a Blood Culture Flask 24 blood culture flasks (BCFs) divided into three groups of 8 were treated as indicated:

Group 1: Piercing of septum with a needle

Group 2: 10^8 CFU/ml broth with *E. coli* swabbed on septum before piercing with a needle Group 3: No piercing of septum A sterile single use needle were used for each BCF.

The BCFs were put into a blood culture cabinet and allowed to stand for five days. No growth were indicated in any of the group 1 or group 3 BCFs. One out of eight BCFs in group 2 became positive within five days, indicating a potential need for decontamination of septa before taking an aliquot if bottle is heavily contaminated (see Table 1).

TABLE 1

| Sample | Piercing of septum with needle | E. coli 10^8 CFU/ml contaminated cap before piercing of septum with needle | No piercing of septum |
|---|---|---|---|
| 1 | Neg | Neg | Neg |
| 2 | Neg | Neg | Neg |
| 3 | Neg | Neg | Neg |
| 4 | Neg | Neg | Neg |
| 6 | Neg | Neg | Neg |
| 7 | Neg | Pos | Neg |
| 8 | Neg | Neg | Neg |

The invention claimed is:

1. A method for detecting and characterizing a microorganism in a clinical sample, said method comprising:
   a) introducing a clinical sample taken from a patient to a first culture vessel containing culture medium;
   b (i)) optionally preculturing said clinical sample in said first culture vessel;
   b (ii)) optionally removing a portion of the clinical sample/medium mixture or, if precultured, the clinical sample culture from said first culture vessel, and introducing said portion to a second culture vessel containing culture medium, and optionally preculturing said portion in said second culture vessel;
   c) removing a test aliquot from said first and/or second culture vessel;
   d) after step c), culturing or continuing to culture said clinical sample and/or portion thereof in said first and/or second culture vessel;
   e) separating DNA from said test aliquot;
   f) performing nucleic acid tests on said DNA to identify the microorganism and to detect the presence or absence of one or more genetic antimicrobial resistance markers in said microorganism, wherein said nucleic acid tests are performed using:
      i) one or more nucleic acid probes and/or primers for microbial identification, a said probe or primer being capable of hybridizing specifically to, or a said primer being capable of selectively amplifying, a nucleotide sequence which is identificatory of a given microorganism; and
      ii) one or more nucleic acid probes and/or primers for antimicrobial resistance marker detection, a said probe or primer being capable of hybridizing specifically to, or a said primer being capable of selectively amplifying, a nucleotide sequence representing a genetic antimicrobial resistance marker;
   and detecting whether or not said probes and/or primers have hybridized to said DNA and/or said primers have been extended; and
   g) performing an antimicrobial susceptibility test using said cultured clinical sample and/or said cultured portion from step (d), without any further sub-culture, wherein microbial growth in said antimicrobial susceptibility test is monitored by assessing growth or markers for growth, wherein the assessment of growth or markers of growth includes obtaining an image of said cultured clinical sample and/or portion, and determining an area of microbial biomass in the image, and wherein the type and concentration of antimicrobial agents used in said antimicrobial susceptibility test is determined by the identity of the microorganism and antimicrobial resistance markers detected in step (f), and optionally continuing to culture said clinical sample and/or portion in said first and/or second culture vessel.

2. The method of claim 1, said method comprising:
   h) providing for, if no microorganism strain is identified in step (f), further culturing said clinical sample to enable further microbial identification and antimicrobial susceptibility tests to be performed to identify the microorganism and determine its antimicrobial resistance profile.

3. The method of claim 1 wherein said clinical sample is from a subject having, suspected of having, or at risk from sepsis; and/or wherein said clinical sample is blood or a blood fraction.

4. The method of claim 1 wherein the culture vessel is a blood culture flask.

5. The method of claim 1 wherein the culture medium contains an agent which neutralizes the presence of any antimicrobial agents present in the clinical sample.

6. The method of claim 1 wherein microbial DNA is selectively separated or enriched from said test aliquot.

7. The method of claim 1 further comprising a step of separating or enriching microorganisms from or in the test aliquot prior to or concurrently with step (d).

8. The method of claim 1, wherein steps (c) to (f) are repeated one or more times.

9. The method of claim 8, wherein steps (c) to (f) are performed without an initial preculture step, and if no microorganism is identified in step (f), steps (c) to (f) are repeated after a preculture step (b).

10. The method of claim 1, wherein the probes or primers of step (f)(i) are designed or selected for the identification of a microorganism in a panel of sepsis-causing microorganisms.

11. The method of claim 1 wherein in step (f) (i) and/or (ii) PCR primers are used.

12. The method of claim 1 wherein in step (f)(i) and/or (ii) hybridization probes are used.

13. The method of claim 12 wherein said hybridization probes are padlock probes comprising 5' and 3' ends that can hybridize to an identificatory or antimicrobial resistance marker nucleotide sequence.

14. The method of claim 13 wherein a circularized padlock probe is detected by rolling circle amplification (RCA).

15. The method of claim 14, wherein the RCA is or comprises circle-to-circle amplification (C2CA) in which a RCA product is cleaved into monomers, and the monomers are circularized and used as templates for a further RCA reaction; and/or
   wherein an RCA product is detected by cleaving the RCA product into monomers, hybridizing said monomers onto an array and detecting the monomers on the array; and/or
   wherein the RCA product is detected microscopically or by imaging or in a flow-cytometry-like method.

16. The method of claim 1, wherein for the nucleic acid tests of step (f) separated DNA is immobilized using capture probes capable of hybridizing to the DNA.

17. The method of claim 1 wherein in step (g) the antimicrobial susceptibility test is performed when a single microorganism is identified in step (f).

18. The method of claim 1 wherein if two or more microorganisms are identified in step (f), the method further comprises further culturing said clinical sample and/or portion to enable further microbial identification and antimicrobial susceptibility tests to be performed to identify the microorganism and determine its antimicrobial resistance profile.

19. A method for detecting and characterizing a microorganism in a clinical sample, said method comprising:
   a) introducing a clinical sample taken from a patient to a first culture vessel containing culture medium;
   b (i)) optionally preculturing said clinical sample in said first culture vessel;
   b (ii)) optionally removing a portion of the clinical sample/medium mixture or, if precultured, the clinical sample culture from said first culture vessel, and introducing said portion to a second culture vessel containing culture medium, and optionally preculturing said portion in said second culture vessel;
   c) removing a first test aliquot from said first and/or second culture vessel;
   d) after step c), culturing or continuing to culture said clinical sample and/or portion thereof in said first and/or second culture vessel;
   e) separating DNA from said first test aliquot;
   f) performing nucleic acid tests on said DNA to identify the microorganism and to detect the presence or absence of one or more genetic antimicrobial resistance markers in said microorganism, wherein said nucleic acid tests are performed using:
      i) one or more nucleic acid probes and/or primers for microbial identification, a said probe or primer being capable of hybridizing specifically to, or a said primer being capable of selectively amplifying, a nucleotide sequence which is identificatory of a given microorganism; and
      ii) one or more nucleic acid probes and/or primers for antimicrobial resistance marker detection, a said probe or primer being capable of hybridizing specifically to, or a said primer being capable of selectively amplifying, a nucleotide sequence representing a genetic antimicrobial resistance marker;

and detecting whether or not said probes and/or primers have hybridized to said DNA and/or said primers have been extended; and
   g) providing an antimicrobial susceptibility test device, which when a microorganism is identified in step (f), performs an antimicrobial susceptibility test using said cultured clinical sample and/or said cultured portion from step (d), without any further sub-culture, wherein microbial growth in said antimicrobial susceptibility test is monitored by assessing growth or markers for growth, wherein the assessment of growth or markers of growth includes obtaining an image of said cultured clinical sample and/or portion, and determining an area of microbial biomass in the image, and wherein the type and concentration of antimicrobial agents used in said antimicrobial susceptibility test is determined by the identity of the microorganism and antimicrobial resistance markers detected in step (f), and optionally continuing to culture said clinical sample and/or portion in said first and/or second culture vessel.

\* \* \* \* \*